US006969782B2

(12) United States Patent
Kisaka et al.

(10) Patent No.: US 6,969,782 B2
(45) Date of Patent: Nov. 29, 2005

(54) METHOD OF PRODUCING TRANSGENIC PLANTS HAVING IMPROVED AMINO ACID COMPOSITION

(75) Inventors: Hiroaki Kisaka, Kawasaki (JP); Takao Kida, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 510 days.

(21) Appl. No.: 09/729,821

(22) Filed: Dec. 6, 2000

(65) Prior Publication Data

US 2004/0093647 A9 May 13, 2004

(30) Foreign Application Priority Data

Dec. 16, 1999 (JP) ............................................. 11-376710

(51) Int. Cl.[7] ........................ C12N 15/82; C12N 15/90; A01H 5/00; A01H 5/10
(52) U.S. Cl. ...................... 800/278; 435/468; 800/287; 800/298
(58) Field of Search ............................... 435/69.1, 410, 435/419, 468; 800/278, 287, 295, 298

(56) References Cited

U.S. PATENT DOCUMENTS

| 5,573,945 A | 11/1996 | Ono et al. ............. 435/252.33 |
| 5,876,983 A | 3/1999 | Sugimoto et al. ........... 435/106 |
| 5,919,694 A | 7/1999 | Sugimoto et al. ...... 435/252.33 |
| 5,998,700 A | 12/1999 | Lightfoot et al. ........... 800/278 |

FOREIGN PATENT DOCUMENTS

| CA | 2180786 | 1/1998 | ........... C12N/15/53 |
| JP | 63-214189 | 9/1988 | ........... C12P/13/14 |
| WO | WO 95/09911 | 4/1995 | ........... C12N/15/00 |
| WO | WO 97/12983 | 4/1997 | ........... C12N/15/53 |

OTHER PUBLICATIONS

An et al., Plant Physiol., 1986, vol. 81, pp. 301–305.*
Van Haaren et al., Plant Mol. Biol., 1991, vol. 17, pp. 615–630.*
L. Camarena, et al., "Transcriptional Repression of GDHA in Escherichia coli is mediated by the NAC Protein", FEMS Microbiology Letters, 167, 1998, pp. 51–56.
A. Ficarelli, et al., "Isolation and Characterization of two CDNA Clones Encoding for Glutamate Dehydrogenase in Nicotiana Plumbaginifolia", Plant Cell Physiol., 40(3), 1999, pp. 339–342.
F. Gallardo, et al., "Changes in Photorespiratory Enzymes and Glutamate Synthases in Ripening Tomatoes", Plant Physiol. Biochem., 1993, 31(2), pp. 189–196.
M. Teige, et al., "Chloroplast Pentose–5–Phosphate 3–Epimerase from Potato: Cloning, CDNA Sequence, and Tissue–Specific Enzyme Accumulation", FEBS Letters, 377, 1995, pp. 349–352.
Herbert N. Arst, Jr., et al., "A Mutant of Aspergillus nidulans Lacking NADP–Linked Glutamate Dehydrogenase," Molec. Gen. Genet. 122, 1973, pp. 261–265.
Alastair R. Hawkins, et al., "Nucleotide Sequence and Regulation of Expression of the Aspergillus nidulans gdhA Gene Encoding NADP Dependent Glutamate Dehydrogenase," Mol. Gen. Genet. 218, 1989, pp. 105–111.
Matthew P. Purnell, et al., "Cloning and Characterisation of a Glutamate Dehydrogenase CDNA from Tomato (Lycopersicon Esculentum L.)," Gene 186, 1997, pp. 249–254.
Kalliopi M. Syntichaki, et al., "The Amino–Acid Sequence Similarity of Plant Glutamate Dehydrogenase to the Extremophilic Archaeal Enzyme Conforms to its Stress–Related Function," Gene 168, 1996, pp. 87–92.
Lynn M. Long, et al., "Assimilatory Glutamate Dehydrogenase (gdhA) Expression in Tobacco," Supplement to Plant Physiology, vol. 108, No. 2, Jun. 1995, ISSN 0032–0889, Abstract.
Lynn M. Long, et al., "Field Evaluation and Nitrogen use Efficiency of Transgenic Tobacco Expressing the Escherichia Coli Glutamate Dehydrogenase Gene," Supplement to Plant Physiology, vol. 111, No. 2, Jun. 1996, ISSN 0032–0889, Abstract.
Lynn M. Long, "Nitrogen Harvest is Increased in gdhA Transgenic Tobacco,"Plant Biology '97 Final Program and Supplement to Plant Physiology, vol. 114, No. 3, Jul. 1997, Abstract.
Rafiqa Ameziane, et al., "Metabolic Engineering of C and N Metabolism with NADP–Glutamate Dehydrogenase," Plant Biology '98 Final Program, 1998, Abstract.

* cited by examiner

Primary Examiner—Ashwin Mehta
(74) Attorney, Agent, or Firm—Oblon, Spivak, McClelland, Maier & Neustadt, P.C.

(57) ABSTRACT

Transgenic plants containing free amino acids, particularly at least one amino acid selected from among glutamic acid, asparagine, aspartic acid, serine, threonine, alanine and histidine accumulated in a large amount, in edible parts thereof, and a method of producing them are provided. In this method, glutamate dehydrogenase (GDH) gene is introduced into a plant together with a regulator sequence suitable for over expressing the sequence encoding GDH gene in plant cells.

26 Claims, 21 Drawing Sheets

FIG. 1

```
gdhA: 1    ATGCTAACCTTCCCGTTGAGCCCGAGTTCGAGCAGGCCTACAAGGAGCTTGCGTCGACC
           ************************************************************
gdh17: 1   ATGCTAACCTTCCCGTTGAGCCCGAGTTCGAGCAGGCCTACAAGGAGCTTGCGTCGACC 61         CTCGAGAACTCCACCCTCTTTGAGCAGCACCCTGAATACCGACGGGCTCTCCAGGTCGTC
           ************************************************************
61         CTCGAGAACTCCACCCTCTTTGAGCAGCACCCTGAATACCGACGGGCTCTCCAGGTCGTC 121        TCCGTTCCCGAGCGCGTTATCCAGTTCCGTGTCGTTTGGGAGAACGACAAGGGCGAGGTT
           ************************************************************
121        TCCGTTCCCGAGCGCGTTATCCAGTTCCGTGTCGTTTGGGAGAACGACAAGGGCGAGGTT 181        CAGATCAACCGCGGTTACCGTGTTCAGTTCAACTCCGCTCTCGGTCCCTACAAGGGTGGT
           ************************************************************
181        CAGATCAACCGCGGTTACCGTGTTCAGTTCAACTCCGCTCTCGGTCCCTACAAGGGTGGT 241        CTCCGTTTCCACCCCTCCGTCAACCTTTCTATCCTGAAGTTCCTTGGCTTCGAGCAGATC
           ************************************************************
241        CTCCGTTTCCACCCCTCCGTCAACCTTTCTATCCTGAAGTTCCTTGGCTTCGAGCAGATC 301        TTCAAAAATGCTCTCACAGGAC[  ◁―――――――  Splicing region
           ********************
301        TTCAAAAATGCTCTCACAGGACGTGCGTAACCGTTACTTCATTGGATGTTTGCCAAGAGT 323              ―――――――▷ ]TAAACATGGGTGGTGGCAAGGGTGGTTCCGACTTCGACCCCAAGG
                          *******************************************
361        ACTAATTGGTATTAGTAAACATGGGTGGTGGCAAGGGTGGTTCCGACTTCGACCCCAAGG 368        GCAAGTCTGACTCTGAAATTCGTCGCTTCTGTACCGCTTTCATGACTGAGCTCTGCAAGC
           ************************************************************
421        GCAAGTCTGACTCTGAAATTCGTCGCTTCTGTACCGCTTTCATGACTGAGCTCTGCAAGC
```

FIG.2

```
428  ACATCGGCGCGGACACTGACCTTCCCGCTGGTGATATCGGTGTTACTGGCCGTGAGGTTG
     ************************************************************
481  ACATCGGCGCGGACACTGACCTTCCCGCTGGTGATATCGGTGTTACTGGCCGTGAGGTTG

488  GTTTCCTTTTCGGCCAGTACCGCAGGATCCGCAACCAGTGGGAGGGTGTTCTCACTGGCA
     ************************************************************
541  GTTTCCTTTTCGGCCAGTACCGCAGGATCCGCAACCAGTGGGAGGGTGTTCTCACTGGCA

548  AGGGTGGCAGCTGGGGTGGTAGCTTGATCCGCCCTGAAGCCACTGGATACGGTGTTGTCT
     ************************************************************
601  AGGGTGGCAGCTGGGGTGGTAGCTTGATCCGCCCTGAAGCCACTGGATACGGTGTTGTCT

608  ACTACGTTCAGCACATGATCAAGCACGTTACCGGTGGAAAGGAGTCCTTCGCAGGCAAGC
     ************************************************************
661  ACTACGTTCAGCACATGATCAAGCACGTTACCGGTGGAAAGGAGTCCTTCGCAGGCAAGC

668  GTGTCGCCATCTCCGGCTCCGGTAACGTTGCCCAGTACGCCGCTCTCAAGGTCATCGAGC
     ************************************************************
721  GTGTCGCCATCTCCGGCTCCGGTAACGTTGCCCAGTACGCCGCTCTCAAGGTCATCGAGC

728  TCGGTGGTTCCGTTGTCTCCCTTTCCGACTCCAAGGGCTCTCTCATTGTCAAGGATGAGT
     ************************************************************
781  TCGGTGGTTCCGTTGTCTCCCTTTCCGACTCCAAGGGCTCTCTCATTGTCAAGGATGAGT

788  CCGCTTCTTTCACCCCTGAAGAGATCGCCCTCATTGCCGACCTCAAGGTTGCCCGCAAGC
     ************************************************************
841  CCGCTTCTTTCACCCCTGAAGAGATCGCCCTCATTGCCGACCTCAAGGTTGCCCGCAAGC

848  AACTCTCCGAGCTCGCCACCTCCTCCGCTTTCGCCGGCAAGTTCACCTACATCCCCGATG
     ************************************************************
901  AACTCTCCGAGCTCGCCACCTCCTCCGCTTTCGCCGGCAAGTTCACCTACATCCCCGATG
```

FIG.3

```
908   CTCGCCCTTGGACCAACATTCCCGGCAAGTTCGAGGTTGCTCTCCCTTCTGCCACTCAGA
      ************************************************************
961   CTCGCCCTTGGACCAACATTCCCGGCAAGTTCGAGGTTGCTCTCCCTTCTGCCACTCAGA

968   ACGAAGTCTCCGGCGAGGAAGCCGAGCACCTCATCAAGTCCGGTGTCCGCTATATTGCTG
      ************************************************************
1021  ACGAAGTCTCCGGCGAGGAAGCCGAGCACCTCATCAAGTCCGGTGTCCGCTATATTGCTG

1028  AGGGTTCCAACATGGGTTGCACCCAGGCCGCCATCGACATCTTTGAGGCTCACCGCAACG
      ************************************************************
1081  AGGGTTCCAACATGGGTTGCACCCAGGCCGCCATCGACATCTTTGAGGCTCACCGCAACG

1088  CCAACCCCGGCGATGCCATCTGGTACGCCCCTGGTAAAGCCGCCAACGCTGGTGGTGTCG
      ************************************************************
1141  CCAACCCCGGCGATGCCATCTGGTACGCCCCTGGTAAAGCCGCCAACGCTGGTGGTGTCG

1148  CCGTCTCTGGTCTTGAGATGGCTCAGAACTCTGCTCGTCTCTCCTGGACATCCGAGGAGG
      ************************************************************
1201  CCGTCTCTGGTCTTGAGATGGCTCAGAACTCTGCTCGTCTCTCCTGGACATCCGAGGAGG

1208  TCGATGCTCGCCTCAAGGGCATCATGGAGGACTGCTTCAAGAACGGTCTCGAGACTGCTC
      ************************************************************
1261  TCGATGCTCGCCTCAAGGGCATCATGGAGGACTGCTTCAAGAACGGTCTCGAGACTGCTC

1268  AGAAGTTCGCTACTCCTGCCAAGGGCGTCCTGCCTTCCCTCGTCACCGGTTCCAACATTG
      ************************************************************
1321  AGAAGTTCGCTACTCCTGCCAAGGGCGTCCTGCCTTCCCTCGTCACCGGTTCCAACATTG

1328  CCGGTTTCACCAAGGTCGCCGAGGCCATGAAGGACCAGGGTGACTGGTGGTGA
      *****************************************************
1381  CCGGTTTCACCAAGGTCGCCGAGGCCATGAAGGACCAGGGTGACTGGTGGTGA
```

— : Splicing region

1. □HindIII marker
2. Non-transgenic tomato no. 1
3. Non-transgenic tomato no. 2
4. pMAT037 no. 1
5. pMAT037 no. 2
6. pMAT037 no. 3
7. AN-gdh-17 no. 6
8. AN-gdh-17 no. 8-2
9. AN-gdh-17 no. 15
10. AN-gdh-17 no. 17
11. 100bp marker 1. -λHindIII marker
2. Non-transgenic tomato no. 1
3. Non-transgenic tomato no. 2
4. pIG121 no. 1
5. pIG121 no. 2
6. pIG121 no. 3
7. T-gdh-4 no. 2
8. T-gdh-4 no. 7-2
9. T-gdh-4 no.9-2
10. T-gdh-4 no. 10
11. 100bp marker 1. 100 bp marker
2. Non-transgenic tomato (leaf)
3. AN-gdh-17 no. 6 (leaf)
4. AN-gdh-17 no. 15 (leaf)
5. AN-gdh-17 no. 6 (fruit)

1. 100 bp marker
2. Non-transgenic-tomato (leaf)
3. T-gdh-4 no. 2 (leaf)
4. T-gdh-4 no. 7-2 (leaf)
5. T-dgh-4 no. 9-2 (leaf
6. T-gdh-4 no. 10 (leaf)
7. T-gdh-4 no. 2 (fruit)
8. T-gdh-4 no. 7-2 (fruit)
9. T-gdh-4 no. 9-2 (fruit)
10. T-gdh-4 no. 10 (fruit)

*AN-gdh-17* gene

*T-gdh-4* gene

Lanes
1. Non-transgenic tomato
2. AN-gdh-17 No.1
3. AN-gdh-17 No.3
4. AN-gdh-17 No.15
5. AN-gdh-17 No.2.1

A. Total DNA(15 μg) was digested with *Bam*HI and *Eco*RI.

B. Total DNA(15 μg) was digested with *Xba*I.

1. Non-transgenic tomato    2. T-gdh No. 1-2
3. T-gdh No. 3-1    4. T-gdh No. 8-1

Total DNA(15 μg) was digested with *Xba*I and *Sac*I.

→ : *T-gdh-4 gene* (1.4 kb)

($n$=3)

(n=3)

1. Non-transgenic potato-1
2. Non-transgenic potato-2
3. Ct-AN-gdh No. 1
4. Mt-dAN-gdh No. 2
5. Mt-dAN-gdh No. 5
6. Mt-dAN-gdh No.8

Total DNA (15 $\mu$ g) was digested with *Eco*RI $(n \geqq 2)$

SEQUENCE LISTING

<160> NUMBER OF SEQ ID NOS: 27

<210> SEQ ID NO 1
<211> LENGTH: 1433
<212> TYPE: DNA
<213> ORGANISM: Aspergillus nidulans

<400> SEQUENCE: 1

```
atgtctaacc ttcccgttga gcccgagttc gagcaggcct acaaggagct tgcgtcgacc      60
ctcgagaact ccaccctctt tgagcagcac cctgaatacc gacgggctct ccaggtcgtc     120
tccgttcccg agcgcgttat ccagttccgt gtcgtttggg agaacgacaa gggcgaggtt     180
cagatcaacc gcggttaccg tgttcagttc aactccgctc tcggtcccta caagggtggt     240
ctccgtttcc accctccgt caacctttct atcctgaagt tccttggctt cgagcagatc     300
ttcaaaaatg ctctcacagg acgtgcgtaa ccgttacttc attggatgtt tgccaagagt     360
actaattggt attagtaaac atgggtggtg gcaagggtgg ttccgacttc gaccccaagg     420
gcaagtctga ctctgaaatt cgtcgcttct gtaccgcttt catgactgag ctctgcaagc     480
acatcggcgc ggacactgac cttcccgctg gtgatatcgg tgttactggc cgtgaggttg     540
gtttcctttt cggccagtac cgcaggatcc gcaaccagtg ggagggtgtt ctcactggca     600
agggtggcag ctggggtggt agcttgatcc gccctgaagc cactggatac ggtgttgtct     660
actacgttca gcacatgatc aagcacgtta ccggtggaaa ggagtccttc gcaggcaagc     720
gtgtcgccat ctccggctcc ggtaacgttg cccagtacgc cgctctcaag gtcatcgagc     780
tcggtggttc cgttgtctcc ctttccgact ccaagggctc tctcattgtc aaggatgagt     840
ccgcttcttt caccctgaa gagatcgccc tcattgccga cctcaaggtt gcccgcaagc     900
aactctccga gctcgccacc tcctccgctt tcgccggcaa gttcacctac atccccgatg     960
ctcgcccttg gaccaacatt cccggcaagt tcgaggttgc tctcccttct gccactcaga    1020
acgaagtctc cggcgaggaa gccgagcacc tcatcaagtc cggtgtccgc tatattgctg    1080
agggttccaa catgggttgc acccaggccg ccatcgacat ctttgaggct caccgcaacg    1140
ccaaccccgg cgatgccatc tggtacgccc ctggtaaagc cgccaacgct ggtggtgtcg    1200
ccgtctctgg tcttgagatg gctcagaact ctgctcgtct ctcctggaca tccgaggagg    1260
tcgatgctcg cctcaagggc atcatggagg actgcttcaa gaacggtctc gagactgctc    1320
agaagttcgc tactcctgcc aagggcgtcc tgccttccct cgtcaccggt tccaacattg    1380
ccggtttcac caaggtcgcc gaggccatga aggaccaggg tgactggtgg tga            1433
```

<210> SEQ ID NO 2
<211> LENGTH: 1240
<212> TYPE: DNA
<213> ORGANISM: Lycopersicon esculentum

<400> SEQUENCE: 2

```
atgaatgctt tagcagcaac aatagaaat tttaagctgg cagctaggct tcttggttta      60
gactcaaagt tggaactaag tctgctaatc cctttcagga aattaaggtg gagtgtacta     120
taccgaagga tgatggcaca ttggcatctt ttgttggatt cagggtacag cacgacaatg     180
cacgagggcc tatgaaaggc ggaatcagat accacccgga ggttgatcct gatgaggtga     240
atgcattagc acagctaatg acatggaaga cagcggtcgc caatattacc atatggtggg     300
gctaaaggag gaataggatg tagtcctagt gacctgagta tctctgagtt ggaacgactt     360
actcgagtat ttactcaaaa aatacatgac ctaatcggaa ttcacaccga tgttcctgca     420
ccagatatgg gaacaaatcc tcagacaatg gcatggattt tagacgagta ctcaaaattt     480
catggttatt cacctgctgt ggtaactgga aaacctgttg atctcggtgg atctctaggc     540
agagatgcag ctactggaag ggggggctct ctttgctaca gaagccctgc ttaatgagca     600
tgggaagagt gttgctggtt cagcgttttg ttatacaggg atttggtaat gttggttcct     660
gggctgcaaa actcatccat gagcaaggtg ggaaagttgt agcagtgagt gacataactg     720
gtgccataaa gaatgagaag ggaatcgaca tagaaagcct attcaaacac gtgaaggaaa     780
ctcgtggagt taaaggtttc catgatgcac atccaattga tgcaaattca atactggtag     840
aagactgtga tgttcttatc ccagctgccc tcggtggagt aatcaacaag gataaccaca     900
aattgaaaat taaagccaaa tatattattg aggctgctaa ccatccaact gatccagaag     960
ctgatgagat ttgtcaaaga aaggagtcac catcctaccg gatatttatg ccaactcggg    1020
tggtgtcacc gtcagttatt ttgagtgggt ccagaacatc caaggcttta tgtgggatga    1080
gaaaaaagtg aatgatgagt tgaagacata catgacaaga ggttttaaag atgtcaagga    1140
tatgtgcaag actcacaact gtgacctccg aatgggcgcc ttcaccttag gtgttaaccg    1200
tgtagctaga gcaaccgttc ttcgaggatg ggaggcgtaa                          1240
```

<210> SEQ ID NO 3
<211> LENGTH: 28
<212> TYPE: DNA
<213> ORGANISM: Artificial Sequence
<220> FEATURE:
<223> OTHER INFORMATION: synthetic DNA

<400> SEQUENCE: 3

```
tctagaatgt ctaaccttcc cgttgagc                                         28
```

<210> SEQ ID NO 4
<211> LENGTH: 28
<212> TYPE: DNA
<213> ORGANISM: Artificial Sequence
<220> FEATURE:
<223> OTHER INFORMATION: synthetic DNA

<400> SEQUENCE: 4

```
gagctctcac caccagtcac cctggtcc                                         28
```

<210> SEQ ID NO 5
<211> LENGTH: 27
<212> TYPE: DNA
<213> ORGANISM: Artificial Sequence
<220> FEATURE:
<223> OTHER INFORMATION: synthetic DNA

<400> SEQUENCE: 5

```
tctagaatga atgctttagc agcaact                                          27
```

<210> SEQ ID NO 6
<211> LENGTH: 27
<212> TYPE: DNA
<213> ORGANISM: Artificial Sequence
<220> FEATURE:
<223> OTHER INFORMATION: synthetic DNA

<400> SEQUENCE: 6
gagctcttac gcctcccatc ctcgaag                                27

<210> SEQ ID NO 7
<211> LENGTH: 28
<212> TYPE: DNA
<213> ORGANISM: Artificial Sequence
<220> FEATURE:
<223> OTHER INFORMATION: synthetic DNA

<400> SEQUENCE: 7
tctagaatgt ctaaccttcc cgttgagc                               28

<210> SEQ ID NO 8
<211> LENGTH: 24
<212> TYPE: DNA
<213> ORGANISM: Artificial Sequence
<220> FEATURE:
<223> OTHER INFORMATION: synthetic DNA

<400> SEQUENCE: 8
cacccatgtt tagtcctgtg agag                                   24

<210> SEQ ID NO 9
<211> LENGTH: 24
<212> TYPE: DNA
<213> ORGANISM: Artificial Sequence
<220> FEATURE:
<223> OTHER INFORMATION: synthetic DNA

<400> SEQUENCE: 9
ctctcacagg actaaacatg ggtg                                   24

<210> SEQ ID NO 10
<211> LENGTH: 28
<212> TYPE: DNA
<213> ORGANISM: Artificial Sequence
<220> FEATURE:
<223> OTHER INFORMATION: synthetic DNA

<400> SEQUENCE: 10
gagctctcac caccagtcac cctggtcc                               28

<210> SEQ ID NO 11
<211> LENGTH: 26
<212> TYPE: DNA
<213> ORGANISM: Artificial Sequence
<220> FEATURE:
<223> OTHER INFORMATION: synthetic DNA

<400> SEQUENCE: 11
ggatccatga atgctttagc agcaac                                 26

<210> SEQ ID NO 12
<211> LENGTH: 26
<212> TYPE: DNA
<213> ORGANISM: Artificial Sequence
<220> FEATURE:
<223> OTHER INFORMATION: synthetic DNA

```
<400> SEQUENCE: 12
tctagataaa ccaagaagcc tagctg                                              26

<210> SEQ ID NO 13
<211> LENGTH: 30
<212> TYPE: DNA
<213> ORGANISM: Artificial Sequence
<220> FEATURE:
<223> OTHER INFORMATION: synthetic DNA

<400> SEQUENCE: 13
ctgcagatgg cttcctcaat tgtctcatcg                                          30

<210> SEQ ID NO 14
<211> LENGTH: 30
<212> TYPE: DNA
<213> ORGANISM: Artificial Sequence
<220> FEATURE:
<223> OTHER INFORMATION: synthetic DNA

<400> SEQUENCE: 14
tctagagcat ctaacgcgtc caccattgct                                          30

<210> SEQ ID NO 15
<211> LENGTH: 26
<212> TYPE: DNA
<213> ORGANISM: Artificial Sequence
<220> FEATURE:
<223> OTHER INFORMATION: synthetic DNA

<400> SEQUENCE: 15
tctagaatga atgctttagc agcaac                                              26

<210> SEQ ID NO 16
<211> LENGTH: 30
<212> TYPE: DNA
<213> ORGANISM: Artificial Sequence
<220> FEATURE:
<223> OTHER INFORMATION: synthetic DNA

<400> SEQUENCE: 16
gggaaggtta gacattaaac caagaagcct                                          30

<210> SEQ ID NO 17
<211> LENGTH: 30
<212> TYPE: DNA
<213> ORGANISM: Artificial Sequence
<220> FEATURE:
<223> OTHER INFORMATION: synthetic DNA

<400> SEQUENCE: 17
aggcttcttg gtttaatgtc taaccttccc                                          30

<210> SEQ ID NO 18
<211> LENGTH: 26
<212> TYPE: DNA
<213> ORGANISM: Artificial Sequence
<220> FEATURE:
<223> OTHER INFORMATION: synthetic DNA

<400> SEQUENCE: 18
gagctcttac gcctcccatc ctcgaa                                              26

<210> SEQ ID NO 19
```

-continued

```
<211> LENGTH: 30
<212> TYPE: DNA
<213> ORGANISM: Artificial Sequence
<220> FEATURE:
<223> OTHER INFORMATION: synthetic DNA

<400> SEQUENCE: 19
ctgcagatgg cttcctcaat tgtctcatcg                                          30

<210> SEQ ID NO 20
<211> LENGTH: 24
<212> TYPE: DNA
<213> ORGANISM: Artificial Sequence
<220> FEATURE:
<223> OTHER INFORMATION: synthetic DNA

<400> SEQUENCE: 20
aaggttagac atgcatctac cgcg                                                24

<210> SEQ ID NO 21
<211> LENGTH: 24
<212> TYPE: DNA
<213> ORGANISM: Artificial Sequence
<220> FEATURE:
<223> OTHER INFORMATION: synthetic DNA

<400> SEQUENCE: 21
cgcgttagat gcatgtctaa cctt                                                24

<210> SEQ ID NO 22
<211> LENGTH: 26
<212> TYPE: DNA
<213> ORGANISM: Artificial Sequence
<220> FEATURE:
<223> OTHER INFORMATION: synthetic DNA

<400> SEQUENCE: 22
gagctcttac gcctcccatc ctcgaa                                              26

<210> SEQ ID NO 23
<211> LENGTH: 26
<212> TYPE: DNA
<213> ORGANISM: Artificial Sequence
<220> FEATURE:
<223> OTHER INFORMATION: synthetic DNA

<400> SEQUENCE: 23
aagcttatat aacccaaaat atacta                                              26

<210> SEQ ID NO 24
<211> LENGTH: 26
<212> TYPE: DNA
<213> ORGANISM: Artificial Sequence
<220> FEATURE:
<223> OTHER INFORMATION: synthetic DNA

<400> SEQUENCE: 24
tctagaggta ccattaattg ctaatt                                              26

<210> SEQ ID NO 25
<211> LENGTH: 21
<212> TYPE: DNA
<213> ORGANISM: Artificial Sequence
<220> FEATURE:
<223> OTHER INFORMATION: synthetic DNA

<400> SEQUENCE: 25
```
cccctcggta tccaattaga g                                                    21

<210> SEQ ID NO 26
<211> LENGTH: 24
<212> TYPE: DNA
<213> ORGANISM: Artificial Sequence
<220> FEATURE:
<223> OTHER INFORMATION: synthetic DNA

<400> SEQUENCE: 26 cgggggtgg gcgaagaact ccag                                                24

<210> SEQ ID NO 27
<211> LENGTH: 1380
<212> TYPE: DNA
<213> ORGANISM: Aspergillus nidulans

<400> SEQUENCE: 27
atgtctaacc ttcccgttga gcccgagttc gagcaggcct acaaggagct tgcgtcgacc           60
ctcgagaact ccaccctctt tgagcagcac cctgaatacc gacgggctct ccaggtcgtc          120
tccgttcccg agcgcgttat ccagttccgt gtcgtttggg agaacgacaa gggcgaggtt          180
cagatcaacc gcggttaccg tgttcagttc aactccgctc tcggtcccta caagggtggt          240 ctccgttttcc acccctccgt caacctttct atcctgaagt tccttggctt cgagcagatc         300
ttcaaaaatg ctctcacagg actaaacatg ggtggtggca agggtggttc cgacttcgac          360
cccaagggca gtctgactc tgaaattcgt cgcttctgta ccgctttcat gactgagctc           420
tgcaagcaca tcggcgcgga cactgacctt cccgctggtg atatcggtgt tactggccgt          480
gaggttggtt tccttttcgg ccagtaccgc aggatccgca accagtggga gggtgttctc          540
actggcaagg gtggcagctg ggtggtagc ttgatccgcc ctgaagccac tggatacggt          600
gttgtctact acgttcagca catgatcaag cacgttaccg gtggaaagga gtccttcgca          660
ggcaagcgtg tcgccatctc cggctccggt aacgttgccc agtacgccgc tctcaaggtc          720
atcgagctcg gtggttccgt tgtctccctt tccgactcca agggctctct cattgtcaag          780
gatgagtccg cttctttcac ccctgaagag atcgccctca ttgccgacct caaggttgcc          840
cgcaagcaac tctccgagct cgccacctcc tccgctttcg ccggcaagtt cacctacatc          900
cccgatgctc gccttggac caacattccc ggcaagttcg aggttgctct cccttctgcc          960
actcagaacg aagtctccgg cgaggaagcc gagcacctca tcaagtccgg tgtccgctat        1020
attgctgagg gttccaacat gggttgcacc caggccgcca tcgacatctt tgaggctcac        1080
cgcaacgcca accccggcga tgccatctgg tacgcccctg gtaaagccgc caacgctggt        1140
ggtgtcgccg tctctggtct tgagatggct cagaactctg ctcgtctctc ctggacatcc        1200
gaggaggtcg atgctcgcct caagggcatc atggaggact gcttcaagaa cggtctcgag        1260
actgctcaga agttcgctac tcctgccaag ggcgtcctgc cttccctcgt caccggttcc        1320
aacattgccg gtttcaccaa ggtcgccgag gccatgaagg accagggtga ctggtggtga        1380

METHOD OF PRODUCING TRANSGENIC PLANTS HAVING IMPROVED AMINO ACID COMPOSITION

BACKGROUND OF THE INVENTION

The present invention relates to transgenic plants having an increased free amino acid content, and a method of producing them. In particular, the present invention relates to transgenic plants containing at least one of asparagine, aspartic acid, serine, threonine, alanine, histidine and glutamic acid accumulated in a large amount, and a method of producing them.

The technique of transforming a plant by introducing a specified gene thereinto, reported for the first time in the world, in the study where it was achieve by introducing a gene into tobacco with *Agrobacterium tumefaciens*, a soil microorganism. Thereafter, many products having useful agricultural characters were produced, and it was also tried to let plants produce useful components. A plant breeding method by such a recombinant DNA technique is considered to be hopeful in place of the ordinary, traditional technique of developing varieties of plants. In this field, improvement in the characteristics of plants concerning nitrogen assimilation is also being studied. The study of amino acids is particularly prospering because they are important ingredients of particularly fruits, root crops and seeds and also they exert a great influence on the tastes of them.

Reports on the biosynthesis of amino acids include, for example, a report that free lysine content of tobacco was increased to 200 times as high content by introduction of *E. coli* DHDPS gene into tobacco (U.S. Pat. No. 5,258,300, Molecular Genetics Res. & Development); a report that free lysine content was increased by introduction of AK gene (EP 485970, WO 9319190); a report that asparagine content was increased to 100 times as high content by introduction of AS gene into tobacco; and a report that tryptophan content was increased to 90 times as high content by introduction of an anthranilic acid-synthesizing enzyme into a rice plant (WO 9726366, DEKALB Genetic Corp). The plants in which a gene is to be induced are not limited to model plants such as tobacco and *Arabidopsis thaliana* but plants which produce fruits such as tomato are also used. For example, as for tomatoes, a transformant thereof was obtained by *Agrobacterium* co-cultivation method in 1986 [S. McCormick, J. Niedermeyer, J. Fry, A. Barnason, R. Horsch and R. Fraley, Plant Cell Reports, 5, 81–84 (1986); Y. S. Chyi, R. A. Jorgenson, D. Goldstern, S. D. Tarksley and F. Loaiza-Figueroe, Mol. Gen. Genet., 204, 64–69 (1986)]. Since then, investigations were made for the improvement of the transgenic plant lines. Various genes relating to the biosynthesis of amino acids and nitrogen assimilation other than those described above are also known. They include asparaginase and GOGAT, and the base sequences of them were also reported.

Glutamic acid which is one of α-amino acids is widely distributed in proteins. It is generally known that a tasty component of tomatoes used as a seasoning and also a tasty component of fermentation products of soybeans (such as soy sauce and fermented soy paste) are glutamic acid. It is also known that glutamic acid is synthesized in the first step of nitrogen metabolism in higher plants. It is also known that glutamine and asparagine formed from glutamic acid are distributed to tissues through phloems and used for the synthesis of other amino acids and proteins. It was reported that in plants, glutamic acid is contained in a high concentration in phloems through which photosynthesis products such as sucrose and amino acids are transported [Mitsuo Chino et al., "Shokubutsu Eiyo/Hiryogaku" p. 125 (1993)]. As for examples of cases wherein glutamic acid is contained in a high concentration in edible parts of plants, it is known that about 0.25 g/100 gf. w. of glutamic acid is contained in tomato fruits ["Tokimeki" No. 2, Nippon Shokuhin Kogyo Gakkaishi, Vol. 39, pp. 64–67 (1992)]. However, glutamic acid of a high concentration cannot be easily accumulated in plant bodies because it is a starting material for amino group-donors and also it is metabolized in various biosynthetic pathways as described above even though the biosynthesizing capacity of the source organs can be improved. As far as the applicant knows, it has never been succeeded to remarkably increase glutamic acid concentration in edible parts of plants by either mated breeding or gene manipulation.

In the first step of the assimilation of inorganic nitrogen into an organic substance, ammonia is incorporated into glutamic acid for mainly forming glutamine. This process is catalyzed by glutamine synthetase (GS). Then glutamine is reacted with α-ketoglutaric acid in the presence of glutamate synthase (GOGAT) to form two molecules of glutamic acid. This GS/GOGAT cycle is considered to be the main pathway of nitrogen assimilation in plants [Miflin and Lea, Phytochemistry 15; 873–885 (1976)]. On the other hand, it is also known that the ammonia assimilation proceeds also through a metabolic pathway other than the pathway wherein ammonia is incorporated in the presence of GS catalyst [Knight and Langston-Unkefer, Science, 241: 951–954 (1988)]. Namely, in this metabolic pathway, ammonia is incorporated into α-ketoglutaric acid for forming glutamic acid. This process is catalyzed by glutamate dehydrogenase (GDH). However, plant GDH has a high Km value for ammonia. The role of this pathway under normal growing conditions has not yet been elucidated enough because ammonia is toxic and the concentration of intracellular ammonia is usually low. A researcher reported that this pathway contributes to the nitrogen assimilation when ammonium concentration in the cells is increased over a normal level (the above-described literature of Knight and Langston-Unkefer).

In plants, glutamate dehydrogenase (GDH) catalyzes a reversible reaction of taking ammonia into α-ketoglutaric acid to form glutamic acid and, on the contrary, deamination from glutamic acid to form α-ketoglutaric acid. It is considered that the former reaction occurs when the amount of ammonia is large, and the latter reaction occurs when nitrogen content is high [Robinson et al., Plant Physiol. 95; 809–816 (1991): and Robinson et al., Plant Physiol. 98; 1190–1195 (1992)]. The directionality of this enzyme is not fixed unlike an enzyme GDH-A which acts in microorganisms to synthesize glutamic acid or an enzyme GDH-B which acts on them to decompose it. In plants, it is considered that there are two kinds of such enzymes, i.e. NADP-depending GDH which functions in chloroplast and NAD-dependent GDH which functions in mitochondria. Since GDH has a high Km value for ammonia and it is highly related to the ammonia level in the photorespiration, it is supposed that NAD-dependent GDH localized in mitochondria has an important role in the assimilation of ammonia [Srivastava and Singh R P, Phytochemistry, 26; 597–610 (1987).

It is known that plant GDH comprises a hexamer composed of two different kinds of polypeptides (α-subunits and β-subunits) linked with each other at random and also that there are seven isozyme patterns depending on the degree of the linkage. After investigations wherein grapevine calli were used, the following facts were reported: When calli cultured in a medium containing a nitrate and glutamic acid were subjected to the electrophoresis, an isozyme comprising β-subunits was increased on the cathodic side. On the contrary, when calli cultured in a medium containing ammonia and glutamine were subjected to the electrophoresis, an isozyme comprising α-subunits was increased on the anodic side. Further, when the calli were transferred from the nitrate medium into the ammonia medium, GDH activity was increased to 3 times as high activity (α-subunits were increased to 4-times and β-subunits were decreased). Thus, the activity moved from the cathodic side to the anodic side [Loulakakis and Poubelakis—Angelakis, Plant Physiol. 97; 104–1111 (1996)]. According to this report, α-subunits were considered to play an important role in the assimilation of ammonia.

Sakakibara et al. [Plant Cell Physiol., 33; 1193–1198] isolated GDH genes from two isozyme bands on the cathodic side in seven isozyme bands in corn roots at the first time in the field of plants in 1995. Thereafter, GDH genes were isolated from grapevine [Syntichaki et al., Gene 168: 87–92 (1996)], *Arabidopsis* [Melo-Olivera et al., Proc. Natl. Acad. Sci., USA 93; 4718–4723 (1996)] and tomato [Purnell et al., Gene 186; 249–254 (1997)]. In particular, the genes isolated from grapevine calli were isolated from an isozyme expressed in ammonia-treated cells, and they are considered to be genes encoding α-subunits. All the genes contain a transit peptide which is functional in mitochondria. GDH genes of corns and tomatoes are expressed in a large amount in their roots, while those of *Arabidopsis* are expressed in the leaves and flowers. It was suggested that only one copy of gene is present in tomato, while two or more genes are present in corn, *Arabidopsis* and grapevine. This fact suggests that also in plants, the constitution and function of genes are different and complicated.

Transgenic plants in which said GDH gene was introduced were also produced. It was reported that when glutamate dehydrogenase GDH (NADP-GDH) gene from *Escherichia coli* was introduced into tobacco and corn for the purpose of imparting resistance to phosphinothricin used as a herbicide, glutamic acid content of the roots of them was increased to 1.3 to 1.4 times as high [Lightfoot David et al, CA 2180786 (1998)]. Namely, according to this report, glutamic acid content of tobacco roots was increased from 14.7 mg/100 gf.w. to 20.6 mg/100 gf. w., and that of corn roots was increased from 16.2 mg/100 gf. w. to 19.1 mg/100 gf w. Although there are other reports on the use of GDH gene, no example is given therein [WO 9509911, α,β-subunits from chlorella (WO 9712983)]. In addition, no analytical value of amino acids of glutamic acid group was given therein.

SUMMARY OF THE INVENTION

The object of the present invention is to provide a method of increasing free amino acid contents of storage organs of plants, in particular, at least one of glutamic acid, asparagine, aspartic acid, serine, threonine, alanine and histidine contained in edible parts including roots and seeds of plants; and also to provide transgenic plants in which free amino acids are accumulated in a large amount.

The object of the present invention is attained by providing a plant having a changed expression level of a major enzyme concerning the assimilation and utilization of nitrogen and/or a plant having an organ-specific expression, and a method of producing such a plant. Such plants can be produced by introducing at least one gene encoding an enzyme which assimilates or utilizes nitrogen together with a suitable regulatory sequence and excessively expressing the same or controlling the expression.

In particular, a transgenic plant in which a free amino acid is accumulated in a large amount, particularly a plant in which at least one of glutamic acid, asparagine, aspartic acid, serine, threonine, alanine and histidine is accumulated in a large amount, can be obtained by introducing a glutamate dehydrogenase (GDH) gene together with a suitable regulatory sequence into the plant.

Therefore, the method of the present invention comprises the step of
a) transforming a plant with a genetic construct containing a sequence causing excessive expression of glutamate dehydrogenase (GDH) and a marker gene;
b) selecting or identifying the transgenic plant based on a character imparted by the marker gene in the genetic construct;
c) screening the transgenic plant in which one or more amino acids are accumulated in a larger amount; and
d) selecting the transgenic plant in which one or more free amino acids are accumulated in a larger amount.

The present invention relates to the manipulation of a gene concerning nitrogen metabolism in plants. In particular, the present invention relates to a method of changing the expression level of an enzyme concerning the assimilation and utilization of nitrogen for the purpose of accumulating a free amino acid, particularly glutamic acid which improves taste, in a large amount in edible parts such as fruits, roots (of root crops) and seeds of useful plants. By increasing, modifying or controlling the expression level of such an enzyme, plants having desired properties can be obtained.

BRIEF DESCRIPTION OF THE DRAWINGS

FIG. 1 shows the nucleotide sequence of glutamate dehydrogenase (GDH) AN-gdh-17 gene from *Aspergillus nidulans* as compared with the known nucleotide sequence of NADP-GDH gene. The upper line shows the nucleotide sequence of NADP-GDH gene (nucleotides 1–427 of SEQ ID NO:27), and the lower line shows that of AN-gdh-17 gene (nucleotides 1–480 of SEQ ID NO:1).

FIG. 2 shows the nucleotide sequence of glutamate dehydrogenase (GDH) AN-gdh-17 gene from *Aspergillus nidulans* as compared with the known nucleotide sequence of NADP-GDH gene (continued from FIG. 1). The upper line shows the nucleotide sequence of NADP-GDH gene (nucleotides 428–907 of SEQ ID NO:27), and the lower line shows that of AN-gdh-17 gene (nucleotides 481–960 of SEQ ID NO:1).

FIG. 3 shows the nucleotide sequence of glutamate dehydrogenase (GDH) AN-gdh-17 gene from *Aspergillus nidulans* as compared with the known nucleotide sequence of NADP-GDH gene (continued from FIG. 2). The upper line shows the nucleotide sequence of NADP-GDH gene (nucleotides 908–1433 of SEQ ID NO:1), and the lower line shows that of AN-gdh-17 gene (nucleotides 961–1380 of SEQ ID NO:27).

In FIG. 4, 35S Pro represents CaMV 35S promoter, and Term represents a terminator.

In FIG. 9, 35S represents CaMV 35S promoter, and Nos represents a Nos-terminator.

FIG. 17A and 17B show the results of Southern analysis of transgenic tomato ($T_1$) with AN-gdh-17 gene of gene of Aspergillus nidulans where FIG. 17A shows the results of Southern analysis with BamHI digestion and FIG. 17B shows the results of Southern analysis with XbaI digestion.

DESCRIPTION OF THE PREFERRED EMBODIMENTS

Figure 4:
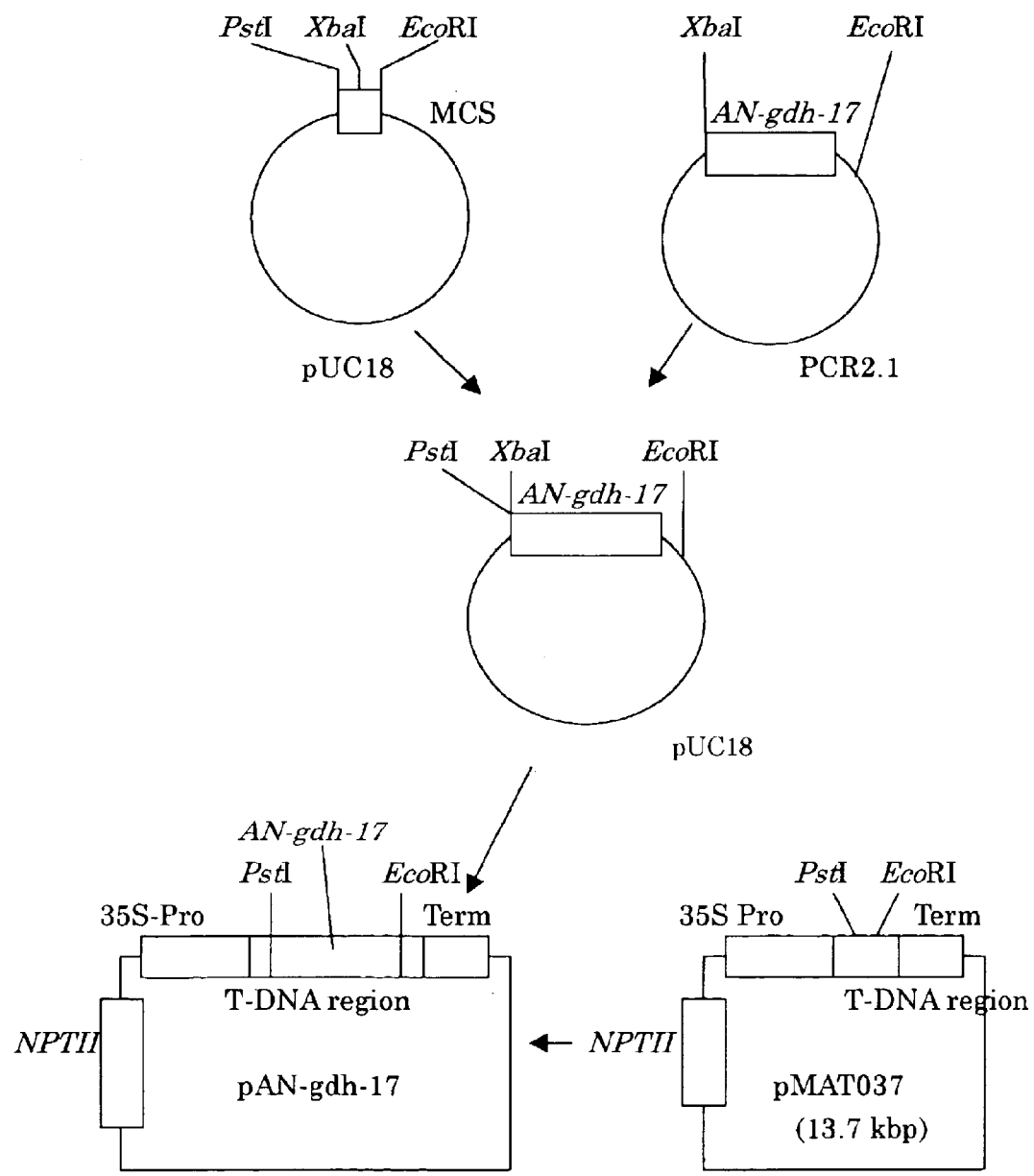
FIG. 4 shows a cloning process of AN-gdh-17 gene into Ti plasmid (pMAT037).

The target genes used in the present invention are those encoding an enzyme concerning the metabolism of ammonia to form amino acids. An example of the target genes is glutamate dehydrogenase (GDH). The expression of this enzyme is enhanced and, in addition, it is modified (for example, ectopic expression by the addition of a transit sequence) to produce a plant having desired properties. As for the manipulation, a plant is transformed with a nucleic acid genetic construct described herein. The transformed plants or their descendants express desired, modified enzymes and they are screened for attaining a change in expression of corresponding mRNA, change in the assimilation or utilization of nitrogen and/or increase in free amino acid content of plants.

In short, the method of the present invention comprises the following steps, and the transgenic plants of the present invention are those produced by this method:
a) the step of cloning an intended gene;
b) the step of, if necessary, recloning the obtained gene into a suitable vector;
c) the step of introducing the vector into plant cells to obtain a transformant; and
d) the step of regenerating the obtained transformant to a plant and cultivating it.

In one of the embodiments of the present invention, one or several genes encoding an enzyme for assimilating or utilizing nitrogen are under the control of a strong constitutive promoter, and over-expressed in the plant bodies. The expression pattern can be modified by the gene manipulation of the plants by utilizing at least one of the followings:
a) a transgene in which a gene sequence encoding an enzyme is linked with a strong constituting promoter in a functional state,
b) a native gene of a many copy number, which encodes a desired enzyme,
c) a regulatory gene for activating the expression of an intended gene for assimilating or utilizing nitrogen.
d) a native gene of multi copy number, which is modified in order to increase the expression and which has a regulatory site, and
e) a transgene which expresses a variant, modified or chimera-type enzyme for assimilating or utilizing nitrogen.

In another embodiment of the present invention, the expression pattern of the enzyme for assimilating or utilizing nitrogen is modified. The expression pattern can be modified by the gene manipulation of the plants by utilizing at least one of the followings:
a) a transgene in which a gene sequence encoding an enzyme is connected to a promoter having a desired expression pattern (such as a promoter having an organ-specific or development stage-specific expression pattern) in a functional state.
b) a modification regulatory gene which activates the expression in a preferred pattern of a gene encoding the enzyme one, and
c) one copy of a native gene which has a regulatory site modified so as to express in a preferred pattern.

In a still preferred embodiment of the present invention, a modified enzyme or enzyme of a different type is represented in a pathway of assimilating or utilizing nitrogen. This embodiment involves the production of a genetic construct which can be expressed in plant cells and which encodes a corresponding enzyme having a catalytic effect different from the catalytic effect of the enzyme which assimilates or utilizes nitrogen in a host plant and also the gene manipulation with the genetic construct. By this technique, plants containing free amino acids in an increased amount can be obtained.

For growing such plants, a conventional method of growing new varieties of plants is unsuitable because it requires screening of large isolated groups and a long time. However, by employing the means of the present invention, such a labor becomes unnecessary and the time can be saved.

The terms and abbreviations used herein are defined as follows:

CaMV35S: cauliflower mosaic virus 35S promoter
NADP-GDH: NADP-dependent glutamate dehydrogenase
NAD-GDH: NAD-dependent glutamate dehydrogenase
Fused gene construct: a genetic construct comprising a promoter in which different genes are connected together (the promoter controls the transcription of heterologous genes)
Heterologous gene: In a genetic construct, a heterologous gene means a gene which is connected with a promoter which is not naturally linked to the gene. The heterologous gene may be from the organism which provide the promoter.
GABA: γ-aminobutyric acid.

The genes of enzymes usable in the present invention can be derived from bacteria, yeasts, alga, animals and plants. They can be obtained also from various other sources. The sequences obtained from those sources can be connected with a suitable promoter which functions in plant cells in such a manner that the function is not disturbed. The alteration by in vitro mutagenesis or de novo synthesis is also possible in order to enhance the translation efficiency in the host plants or to change the catalytic effect of the encoded enzyme. The alteration includes the modification of the residue concerning the active center but is not limited thereto. The inducible gene can be modified so as to have an optimum codon depending on the codon usage of the host or the organelle to be expressed. If necessary, such a gene sequence can be linked with a nucleic acid sequence encoding a suitable transit peptide.

A preferred alteration also includes a construction of a hybrid enzyme. For example, different domains of related enzymes obtained from the same or different organisms can be combined with each other to obtain an enzyme having a new property.

In addition, nucleic acid segments capable of hybridizing with the above-described various nucleic acid sequences under stringent conditions can also be used in the present invention so far as the desired activity is not lost. Thus, nucleic acid segments encoding a protein, in which one or more amino acids are deleted, added or replaced, are also included. The term "stringent conditions" indicates ordinary conditions well known by those skilled in the art such as described by Sambrook et al [as described above (1989)]. Nucleic acid sequences capable of hybridizing under such conditions will usually have at least 60%, preferably at least 80% and particularly preferably at least 90% of homology to each other.

Various genes are included in the enzyme genes for assimilating or utilizing nitrogen usable in the present invention. Glutamate dehydrogenase (GDH) gene is one of examples of preferred enzymes usable for accumulating glutamic acid. When GDH gene is used, it is expressed in sense direction. When GDH gene is selected, it is preferably expressed as a fusion gene having a transit peptide bonded to 5' side thereof. Particularly preferred transit peptides are transit peptide for mitochondria and that for chloroplast.

A preferred embodiment of the present invention will be illustrated with reference to an example wherein a tomato plant is manipulated by a genetic engineering technique with a recombinant genetic construct encoding NADP-dependant GDH gene from a fungus (*Aspergillus nidulans*) [Mol. Gen. Genetics, 218, 105 (1989)] or tomato NAD-dependant GDH gene [Purnell et al., Gene 186; 249–254 (1997)] functionally connected to the cauliflower mosaic virus (CaMV) 35S promoter which is a powerful constitutive plant promoter. In the lines wherein GDH is excessively expressed, free amino acid content is increased as compared with that of the parent plant used as the control. In particular, glutamic acid content is increased to twice or three times as much amount.

The nucleic acid constructs usable in the present invention can be prepared by a method well known by those skilled in the art. For example, the details of a method wherein the genetic construct is divided into genes and the properties of them are determined and also a recombinant DNA method which can be employed for the operation and the preparation of the genetic construct itself are described in, for example, Sambrook et al., Molecular cloning-Laboratory manual, the second edition (Cold Spring Harbor Laboratory Press). When a nucleotide sequence of a desired component is known, it is advantageous not to isolate it from a biological source but to synthesize it. In such a case, those skilled in the art can refer to literatures such as Caruthers et al., Nuc. Acids. Res. Symp. Ser. 7: 215–233 (1980) and Chow and Kempe, Nuc. Acids. Res. 9: 2807–2817 (1981). In other cases, the intended component can be advantageously produced by polymerase chain reaction (PCR) amplification. As for PCR method, those skilled in the art can refer to Gelfand, "PCR Technique (The Theory and Application of DNA Amplification)" edited by H. A. Erlich and published by Stockton Press, New York in 1989 and "Present Protocol in Molecular Biology" Vol. 2, Chapter 15 edited by Ausubel et al., and published by John Wiley & Sons in 1988.

The genetic constructs used in the present invention may generally contain a suitable promoter which functions in plant cells, a suitable terminator such as nopaline synthetic enzyme gene terminator, other elements useful for regulating the expression and marker genes suitable for selecting the transformant such as drug-resistant genes, e. g. genes resistant to kanamycin, G 418 or hygromycin in addition to the intended gene. The promoter contained in the genetic construct may be a constitutive promoter, organ-specific promoter or developmental stage-specific promoter. The promoter can be suitably selected depending on the host, gene, desired expression level, organ for the expression, developmental stage, etc.

According to the present invention, a plant showing an excess expression of an enzyme for assimilating or utilizing nitrogen can be obtained by transforming plant cells with a genetic construct containing a plant promoter linked with a sequence encoding a desired enzyme. In a preferred embodiment of the present invention, related promoters are powerful, organ-unspecific or developmental stage-unspecific promoters (such as promoters which strongly express in many or all tissues). An example of such powerful, constitutive promoters is CaMV35S promoter.

In another embodiment of the present invention, it is advantageous in some cases that a plant is manipulated with a genetic construct in which an organ-specific or growing stage-specific promoter is linked with a sequence encoding a desired enzyme. For example, when the expression in a photosynthetic tissues and organs is intended, a promoter of ribulose bisphosphate carboxylase (RuBisCO) gene or chloroplast a/b linked protein (CAB) gene is usable. When the expression in seeds is intended, promoters of various seed storage protein genes are usable. When the expression in fruits is intended, a fruit-specific promoter (such as tomato 2A11) is usable. When the expression in tubers is intended, a promoter of protein genes stored in tubers (such as potato patatine) is usable.

In still another embodiment of the present invention, it can be advantageous to transform a plant with a genetic construct obtained by linking a derived promoter with a sequence encoding a desired enzyme. Examples of such promoters are various. They include heat shock genes, protection responding genes (such as phenylalanine ammonia lyase genes), wound responding genes (such as cell wall protein genes rich in hydroxyproline), chemically inducible genes (such as nitrate reductase genes and chitinase genes) and dark inducible genes (such as asparagine synthetase genes (Coruzzi and Tsai, U.S. Pat. No. 5,256,558). However, these promoters are not limited to them.

The recombinant nucleic acid genetic construct of the present invention may contain a marker which can be selected for tracing the transmission of the genetic construct. For example, a genetic construct transmitted in bacteria preferably contains an antibiotic-resistant gene such as kanamycin resitant, tetracycline resitant, streptomycin resistant or chloramphenicol resitant genes. The vectors which transfer the genetic construct include plasmid, cosmid, bacteriophage and viruses. In addition, the recombinant genetic construct may contain a marker gene which can be selected or a marker gene which can be screened, which genes can be expressed for a plant for isolating, identifying or tracing the plant cells transformed with the genetic construct. The selective markers include genes which impart resistance to an antibiotic (such as kanamycin or hygromycin) or resistance to a herbicide (such as sulfonylurea, phosphinothricin or glyphosate). However, the markers are not limited to them. The markers which can be screened include genes encoding β-glucuronidase [Jefferson, Plant Mol. Biol. Rep 5: 387–405 (1987)], genes encoding luciferase [Ow et al., Science 234: 856–859 (1986)] and B and Cl gene products controlling the production of anthocyanin pigment. However, these examples are not to limit the markers.

The gene-introducing method which can be employed in the present invention is not particularly limited. Any method known in the art for transferring a gene into plant cells or plant bodies can be employed. For example, in an embodiment of the present invention, *Agrobacterium* can be used for introducing a genetic construct into a plant. In such a transformation, it is desirable to use binary *Agrobacterium* T-DNA vector [Bevan, Nuc. acid Res. 12: 8711–8721 (1984)] and co-culture manipulation [Horsch et al, Science, 227: 1229–1231 (1985)]. *Agrobacterium* transformed plant line is usually used for manipulating dicotyledons [Bevans et al., Ann. Rev. Genet., 16: 357–384 (1982); and Rogers et al., Methods Enzymol., 118: 627–641 (1986)]. *Agrobacterium* transformed plant line is also usable for transforming monocotyledons and plant cells [Hernalsteen et al., EMBO J., 3: 3039–3041 (1984); Hoykass-Van Slogteren et al., Nature, 311: 763–764 (1984); Grimsley et al., Nature, 325: 167–1679 (1987); Boulton et al., Plant mol. Biol., 12: 31–40 (1989); and Gould et al., Plant Physiol., 95: 426–434 (1991)]. When the *Agrobacterium* system is used for the transformation of plants, the recombinant DNA genetic construct further contains at least right border sequence of T-DNA site at a position adjacent to DNA sequence to be introduced into plant cells. In a preferred embodiment, the sequence to be introduced is inserted between the left and right T-DNA border sequences. Suitable design and construction of transformed vectors based on T-DNA are well-known in the art.

In another embodiment, various methods other than those described above can be employed for introducing the recombinant nucleic acid genetic construct into plants and plant cells. An example of other gene introduction method and transformation method is a protoplast transformation of naked DNA by calcium, polyethylene glycol (PEG) or electroporation [Paszkowski et al., EMBO J., 3: 2717–2722 (1984); Potrykus et al., Mol. Gen. Genet., 199: 169–177 (1985); Fromm et al., Proc. Nat. Acad. Sci. USA, 82: 5824–5828 (1985); and Shimamoto et al., Nature, 338: 274–276 (1989)]. According to the present invention, various plants and plant cells can be manipulated to obtain desired physiological properties described herein from by using the nucleic acid construct and the transformation method, as described above. The methods of the present invention are particularly advantageous when the target product is a monocotyledon or plant cells. In a preferred embodiment, the target plants and plant cells to be manipulated are, for example, tomatoes, potatoes, beets, soybeans, *Arabidopsis*, corns, wheats, rice plants and sugar canes.

According to the present invention, an intended plant can be obtained by introducing and manipulating a genetic construct as disclosed herein into various plant cells of, for example, protoplasts, tissue-cultured cells, tissues and organ explants, pollens, embryos and whole plant bodies. From the plants manipulated according to the embodiment of the present invention, the intended transgenic plant is selected or screened by an approach and method described below. An individual plant can be regenerated from the isolated transformant. Methods of regenerating various kinds of individual plants from plant cells, tissues or organs are known by those skilled in the art.

The transformed plant cells, calli, tissues or plants can be identified and isolated by selecting or screening the characters encoded by marker genes contained in the genetic construct used for the transformation. For example, the selection can be conducted by growing a manipulated plant in a medium containing an repressive amount of antibiotic or herbicide to which the introduced genetic construct can impart the resistance to the manipulated plant. Further, the transformed plant cells and plants can be identified by the screening with reference to the activity of visible marker genes (such as β-glucuronidase genes, luciferase genes, B genes or Cl genes) which can be present in the transgenic nucleic acid construct of the present invention. The methods of the selection and screening are well known by those skilled in the art.

Physical methods and biochemical methods can be employed for identifying plants containing the genetic construct of the present invention or plant cells transformed with the construct. Examples of the methods are as follows:

1) Southern analysis or PCR amplification for detecting and determining the structure of recombinant DNA insert;
2) Northern blotting, S1 RNase protection, primer elongation PCR amplification or reverse transcriptase PCR (RT-PCR) amplification for detecting for determining the RNA transcription product of genetic construct; and
3) When the genetic construct is a protein, protein gel electrophoresis, western blotting, immune precipitation, enzyme immunoassay, etc. can be employed. These assay methods are well known by those skilled in the art.

In the present invention, the transformed plant can be screened for an intended physiological change for the purpose of obtaining the plant having improved component characters. For example, when the manipulation is conducted for excessive expression of GDH enzyme, the transformed plant can be tested in a desired growing stage in which it expresses GDH enzyme and a desired tissue in a desired growing stage. Then the plant having a desired physiological change, such as excessive expression of GDH gene, can be successively screened with reference to a desired change in the components.

According to the present invention, plants manipulated by modifications in the process for assimilating or utilizing nitrogen have improved component characteristics. Namely, they contain a large amount of free amino acids, particularly glutamic acid, asparagine, aspartic acid, serine, threonine, alanine and histidine. Among these amino acids, glutamic acid usable as a tasty component is contained in a particularly large amount. The manipulated plants and plant lines having such improved characters can be identified by determining free amino acid contents of the plants. The operation and method of the analysis are well known by those skilled in the art.

The plants obtained by the present invention have free amino acid contents higher than those of control plants (parent plants). In a preferred embodiment, free amino acid content, particularly glutamic acid (tasting component) content in edible parts such as fruits, roots and seeds of a desired plant is increased to at least twice as high as that of the parent. The total amino acid content is also increased to 2 to 4 times as high as that of the parent. As for amino acids other than glutamic acid, the increase in amount of particularly aspartic acid, asparagine, alanine, serine, threonine and histidine is remarkable.

The following Examples relating to the production of plants by the manipulation of excessive expression of NADP-GDH gene or NAD-GDH gene will concretely illustrate the present invention in detail. It should be understood that the scope of the present invention is not limited to the following examples.

EXAMPLE 1

Isolation of GDH Gene from *Aspergillus nidulans* and Tomato, and Construction of Ti Plasmid (1) Isolation of NADP-Dependent GDH Gene (AN-gdh-17) from *Aspergillus nidulans* and NAD-Dependent GDH Gene (T-gdh-4) from Tomato:

*A. nidulans* was cultured on potato dextrose agar medium at 30° C. overnight. The colonies thus obtained were further cultured in a dextrose liquid medium for 2 days. Total RNA was produced from the propagated microbes.

The inorganic salt of MS medium [Murashige and Skoog, Physiol. Plant., 15: 473–479 (1962)] (Wako Pure Chemical Industries, Ltd.) and MS vitamin were used for tomato seeds. At first, tomato seeds surface-sterilized with 70% ethanol (30 seconds) and 2% sodium hypochlorite (15 minutes) were placed on plant hormone-free MS agar medium, and cultured at 25° C. for one week while the daylight hours were kept to be 16 hours to obtain sterile plants. Total RNA was prepared from the roots of the obtained seedlings.

As for the total RNA, mRNA was purified with Poly (A) Quick mRNA Isolation Kit (Stratagene Co.) and then First-Strand cDNA was produced with First-Strand cDNA Synthesis Kit (Amersham Pharmacia Biotech Co.). The PCR reaction was conducted with First-Strand cDNA, thus obtained, as a template. The PCR reaction was conducted with PCR system 2400 (Perkin Elmer) as follows: 35 cycles under conditions of 94° C.—3 minutes, 94° C.—45 seconds, 59° C.—30 seconds, 72° C.—90 seconds; and then 72° C.—10 minutes. The primers used are shown in Table 1. As a result, a band of about 1.4 kbp from *A. nidulans* and that of about 1.2 kb from tomato were amplified and they were coincident with the expected sizes of the intended genes. Obtained PCR products were cloned with TA-cloning kit (Invitrogen Co.).

The sequences of 2 clones of plasmids obtained by cloning *A. nidulans* gene of an intended size and also the sequences of 5 clones of plasmids obtained by cloning a tomato root gene of an intended size were determined with a sequencer (377A of ABI Co.), and the homology of them to known NAFP-dependent GDH gene from *A. nidulans* [Alastair et al., Mol. Gen. Genet. 218; 105–111 (1989)] and GDH gene from tomato [Purnell et al., Gene 186; 249–254 (1997)] was examined.

The nucleotide sequence of one of two clones from *A. nidulans* (AN-gdh-17-SEQ ID NO:1) coincided with known nucleotide sequence of NADP-GDH gene (SEQ ID NO:27) (FIG. 1-3). However, it was found that in two splicing sites, one splicing site of about 50 bp remained in the gene. Because *A. nidulans* has eucaryote-type splicing recognition site, the experiment in the subsequent step was conducted as it was. On the other hand, nucleotide sequences of 2 clones (T-gdh-4 and T-gdh-22) in 5 tomato root clones coincided with a known legdh I sequence. The nucleotide sequence of AN-gdh-17 is shown in SEQ ID NO:1, and that of T-gdh-4 is shown in SEQ ID NO:2.

TABLE 1

Primer DNA used for PCR reaction a. 5'-region-TCT AGA ATG TCT AAC CTT CCC GTT GAG C-3'-region   (28 mer)   (SEQ ID:3)
   5'-region-GAG CTC TCA CCA CCA GTC ACC CTG GTC C-3'-region   (28 mer)   (SEQ ID:4)

b. 5'-region-TCT AGA ATG AAT GCT TTA GCA GCA ACT-3'-region   (27 mer)   (SEQ ID:5)
   5'-region-GAG CTC TTA CGC CTC CCA TCC TCG AAG-3'-region   (27 mer)   (SEQ ID:6)

a. NADP-GDH gene specific primer [Alastair et al. Mol. Gen. Genet., 218; 105–111 (1989), PCR product, about 1.4 kbp]

b. legdh 1 specific primer [Purnell et al., Gene 186; 249–254 (1997), PCR product, abut 1.2 kbp]

(2) Subcloning of AN-gdh-17 Gene into Ti-Plasmid (pMAT037):

AN-gdh-17 gene cloned into PCR2.1 vector was subcloned into Ti plasmid (pMAT037) which was a plant transformation vector [Matsuoka and Nakamura, Proc. Natl. Acad. Sci. USA, 88: 834–838 (1991)]. Because pMAT037 did not have restriction enzyme sites suitable for the direct insertion, the gene was once ligated into pUC18 (XbaI, EcoRI site used) to transform *E. coli* JM109. It was then ligated with Ti plasmid through PstI site and EcoRI site in pUC18 to obtain plasmid pAN-gdh-17 (FIG. 3 and Table 2). The transformation into *E. coli* DH5α was conducted. *Agrobacterium* strain EHA101 was transformed with Ti plasmid in which AN-gdh-17 had been introduced. Obtained *Agrobacterium* pAN-gdh-17/EHA101 was used for the infection of tomatoes.

(3) Construction of pCt-AN-gdh, pCt-dAN-gdh and pMt-dAN-gdh:

NADP-GDH gene from *Aspergillus nidulans* has naturally two splicing sites. Although these splicing sites should have been removed by the amplification of GDH gene with cDNA by PCR method, AN-gdh-17 gene obtained in the experiment still had one splicing site of about 50 bp remaining therein (FIG. 1, see nucleotide sequence). Therefore, the remaining nucleotide sequence of about 50 bp was removed by PCR method.

Figure 6:
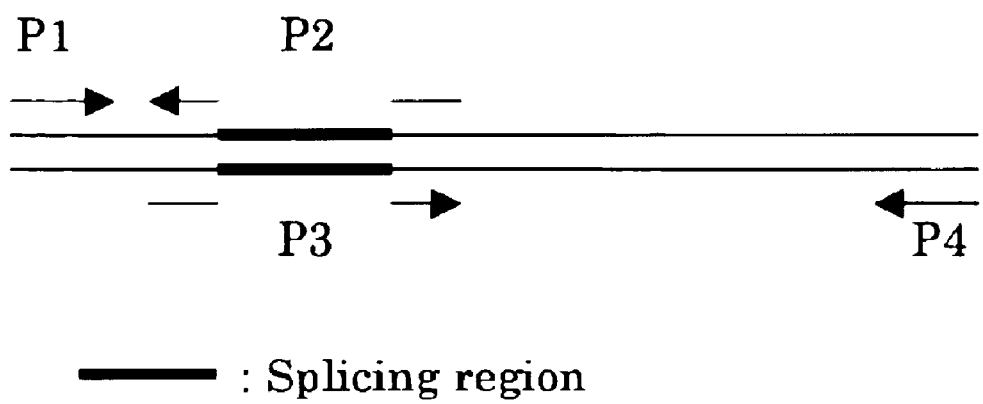
FIG. 6 is a schematic diagram of a process for removing a splicing region from NADP-GDH gene, wherein thick lines show the splicing region, and P1 through P-4 each represent a PCR primer.

The process for the construction of these genetic constructs is shown in FIG. 6. In this process, DNA segments were amplified by PCR method by using primer P1 containing 5' terminal of the cloned gene sequence, primer 2 containing 5' side and 3' side of the splicing site but free of the splicing site, primer P3 containing 5' side and 3' side of the splicing site but free of the splicing site, and primer P4 containing 3' terminal of AN-gdh-17 gene and also using AN-gdh-17 as the template. Then the size of the PCR product was confirmed by the electrophoresis and the product was re-extracted from the gel. The re-extracted PCR products were mixed together. PCR reaction was conducted again by using primers P1 and P4. The obtained PCR products were cloned and sequenced to confirm that the splicing site was accurately removed.

The sequences of the above-described P1 to P4 were as follows:

```
P1;  5'-TCTAGAATGTCTAACCTTCCCGTTGAGC-3'   (SEQ ID:7)

P2;  5'-CACCCATGTTTAGTCCTGTGAGAG-3'      (SEQ ID 8)

P3;  5'-CTCTCACAGGACTAAACATGGGTG-3'      (SEQ ID:9)

P4;  5'-GAGCTCTCACCACCAGTCACCCTGGTCC-3'  (SEQ ID:10)
```

Figure 5:
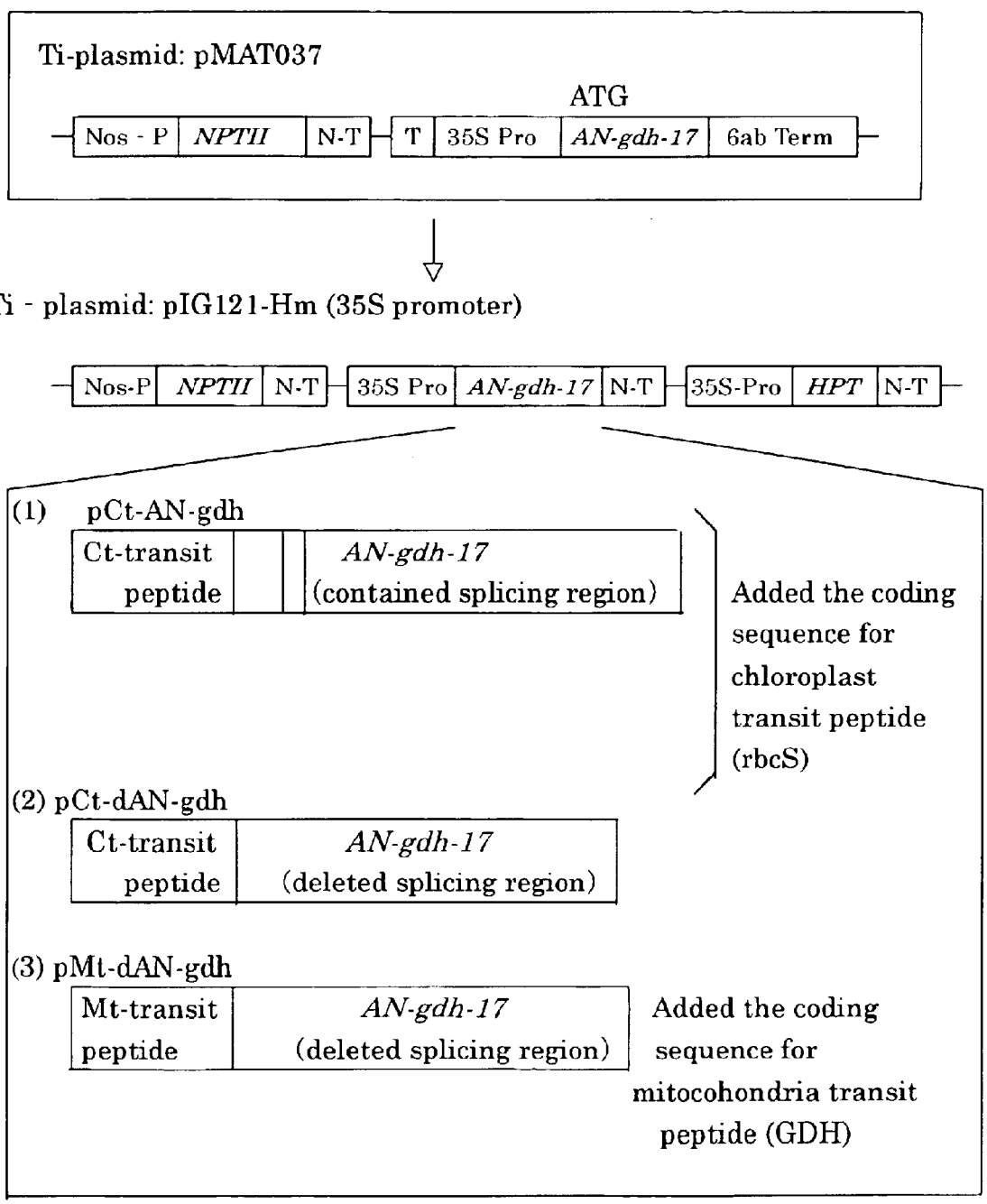
FIG. 5 is a schematic view showing a process for constructing a genetic construct containing a sequence encoding NADP-GDH A gene from *Aspergillus* and connected to a transit peptide, i. e. pCt-AN-ghd, pCt-dAN-gdh and pMt-dAN-gdh, and the structures of them.

Thus, dAN-gdh-17 gene from which the splicing site had been removed was obtained (Table 2, FIG. 5).

To make the action of the introduced gene more functional at a suitable position, the transit peptide sequence for mitochondria or chloroplast was connected to the upstream of the initiation codon of AN-gdh-17 gene or dAN-gdh-17 gene (Table 2, FIG. 5). As for the peptide sequences used, a nucleotide sequence (about 70 bp) added to tomato GDH gene was used as the transit peptide sequence for mitochondria, and a nucleotide sequence (about 120 bp) added to the small subunit gene of tomato RuBisCO was used as the transit peptide sequence for chloroplast. These genes were linked with AN-gdh-17 gene or dAN-gdh-17 gene by PCR method. The transit peptide sequence for mitochondria was obtained by using two primers(5'-GGATCCATGAATGCTTTAGCAGCAAC-3': sequence SEQ ID:11, and 5'-TCTAGATAAACCAAGAAGCCTA-GCTG-3': sequence SEQ ID:12) by PCR. The transit peptide sequence for chloroplast was obtained by using two primers (5'-CTGCAGATGGCTTCCTCAATTGTCTCATCG-3': sequence SEQ ID:13, and 5'-TCTAGAGCATCTAACGC-GTCCACCATTGCT-3': sequence SEQ ID: 14) by PCR.

Figure 7:
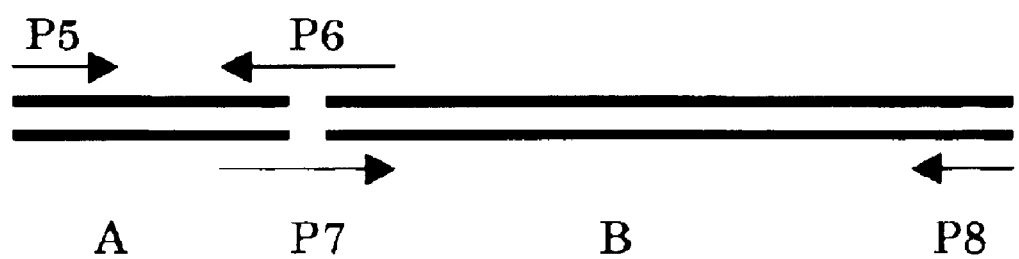
FIG. 7 is a schematic diagram showing a process for linking a transit peptide sequence with Aspergillus NADP-GDH A gene sequence, wherein A represents nucleotide sequence of a transit peptide, B represents a nucleotide sequence of AN-gdh-17 gene, and P5 through P8 each represent a PCR primer.

These transit peptide sequences were linked with AN-gdh-17 gene or dAN-gdh-17 gene as shown in FIG. 7. Namely, the respective DNA segments were amplified by using primer P5 corresponding to 3' side of the transit peptide, primer P6 containing the sequence of 3' terminal of the transit peptide and the sequence at 5' terminal of AN-gdh-17 gene or dAN-gdh-17 gene, primer P7 containing sequences of 3' terminal of the transit peptide and 5' terminal of AN-gdh-17 gene or dAN-gdh-17 gene, and primer P8 containing sequences of 3' terminal of AN-gdh-17 gene or dAN-gdh-17 gene. Then the size of the PCR product was confirmed by the electrophoresis. After the extraction from the gel, the extracted segments were mixed together and again subjected to PCR with primers P5 and p8. The amplified segments were cloned and then sequenced to confirm that the base sequence of the transit peptide was correctly added to AN-gdh-17 gene or dAN-gdh-17 gene.

The sequences of P5 to P8 are as shown below.

In the primer used for linking with the transit peptide sequence for mitochondria:

```
P5; 5'-TCTAGAATGAATGCTTTAGCAGCAAC-3'      (SEQ ID:15)

P6; 5'-GGGAAGGTTAGACATTAAACCAAGAAGCCT-3' (SEQ ID:16)

P7; 5'-AGGCTTCTTGGTTTAATGTCTAACCTTCCC-3' (SEQ ID:17)

P8; 5'-GAGCTCTTACGCCTCCCATCCTCGAA-3'     (SEQ ID:18)
```

In the primer used for linking with the transit peptide sequence for chloroplast:

```
P5; 5'-CTGCAGATGGCTTCCTCAATTGTCTCATCG-3' (SEQ ID:19)

P6; 5'-AAGGTTAGACATGCATCTACCGCG-3'       (SEQ ID:20)

P7; 5'-CGCGTTAGATGCATGTCTAACCTT-3'       (SEQ ID:21)

P8; 5'-GAGCTCTTACGCCTCCCATCCTCGAA-3'     (SEQ ID:22)
```

AN-gdh-17 gene was introduced into the sense direction in the multicloning site of Ti plasmid pMAT037 (FIG. 3). In the construction of pCt-AN-gdh, pCt-dAN-dgh and pMt-dAN-gdh, the cloning was conducted with Ti plasmid pIG121-Hm and the gene was introduced in order to compare the effect obtained by using CaMV35S promoter with that obtained by using fruit-specific promoter gene (2A11) which will be described below (Table 2, FIG. 5).

(4) Genetic construction with fruit-specific promoter (2A11 promoter)

Fruit-specific expression promoter (2A11) was obtained by PCR method by using total DNA obtained from tomato seedlings as the template. In the primers (SEQ ID:23 and 24) used, the sequences of restriction enzyme sites, HindIII and XbaI used for the introduction into Ti plasmid were designed respectively.

The sequences of the primers were as follows:

```
5'-AAGCTTATATAACCCAAAATATACTA-3'    (SEQ ID:23)

5'-TCTAGAGGTACCATTAATTGCTAATT-3'    (SEQ ID:24)
```

Figure 8:
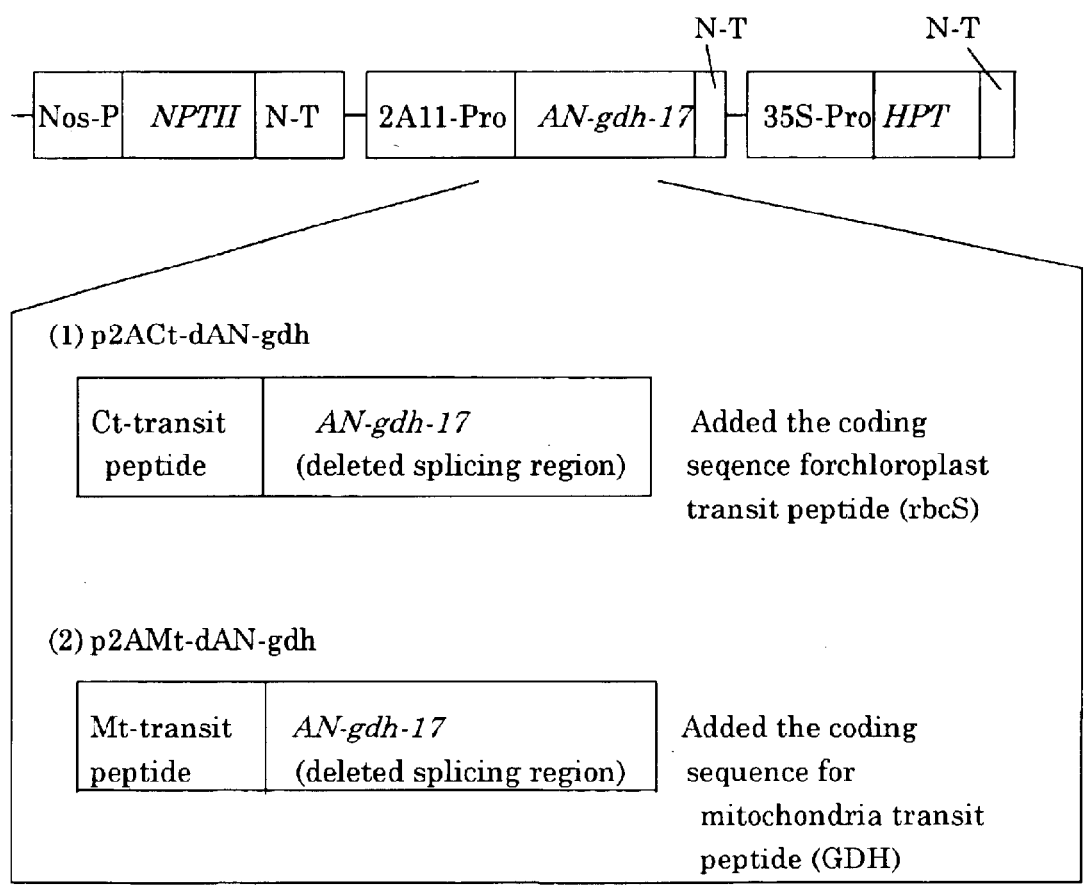
FIG. 8 is a schematic diagram showing the structures of genetic constructs p2ACt-dAN-gdh and p2AMt-dAN-gdh containing NADP-GDH gene from Aspergillus nidulans connected with 2A11 promoter.

After cloning the obtained PCR product with TA cloning kit, the nucleotide sequence thereof was confirmed by the sequence analysis. Obtained 2A11 promoter was replaced with CaMV35S promoter before GUS gene of Ti plasmid pIG121-Hm by using the above-described restriction enzymes, HindIII and XbaI. Then GUS part was replaced with Ct-dAN-gdh gene or Mt-dAN-gdh gene. The process for the replacement with Ct-dAN-gdh gene or Mt-dAN-gdh gene was the same as that employed for CaMV35S promoter. From them, plasmids p2Act-dAN-gdh and p2AMt-dAN-gdh were obtained (FIG. 8).

Important structures of plasmids produced as described above are summarized in following Table 2.

TABLE 2

Constructions of Ti-plasmid vectors containing AN-gdhA gene.

| | AN-gdhA Splicing region | | Transit peptide | | | Promoter. | |
|---|---|---|---|---|---|---|---|
| | Contain | Delete | No | Chl.*1 | Mit.*2 | 35S | 2A11 |
| pAN-gdh-17 (FIG. 4) | ○ | | ○ | | | ○ | |
| pCt-AN-gdh (FIG. 5) | ○ | | | ○ | | ○ | |
| pCt-dAN-gdh (FIG. 5) | | ○ | | ○ | | ○ | |
| pMt-dAN-gdh (FIG. 5) | | ○ | | | ○ | ○ | |
| p2ACt-dAN-gdh (FIG. 8) | | ○ | | ○ | | | ○ |
| p2AMt-dAN-gdh (FIG. 8) | | ○ | | | ○ | | ○ |

Chl.*1: Chloropoast,
Mit.*2: Mitochondria (5) Subcloning of T-gdh-4 Gene into Ti Plasmid (pIG121-Hm)

Figure 9:
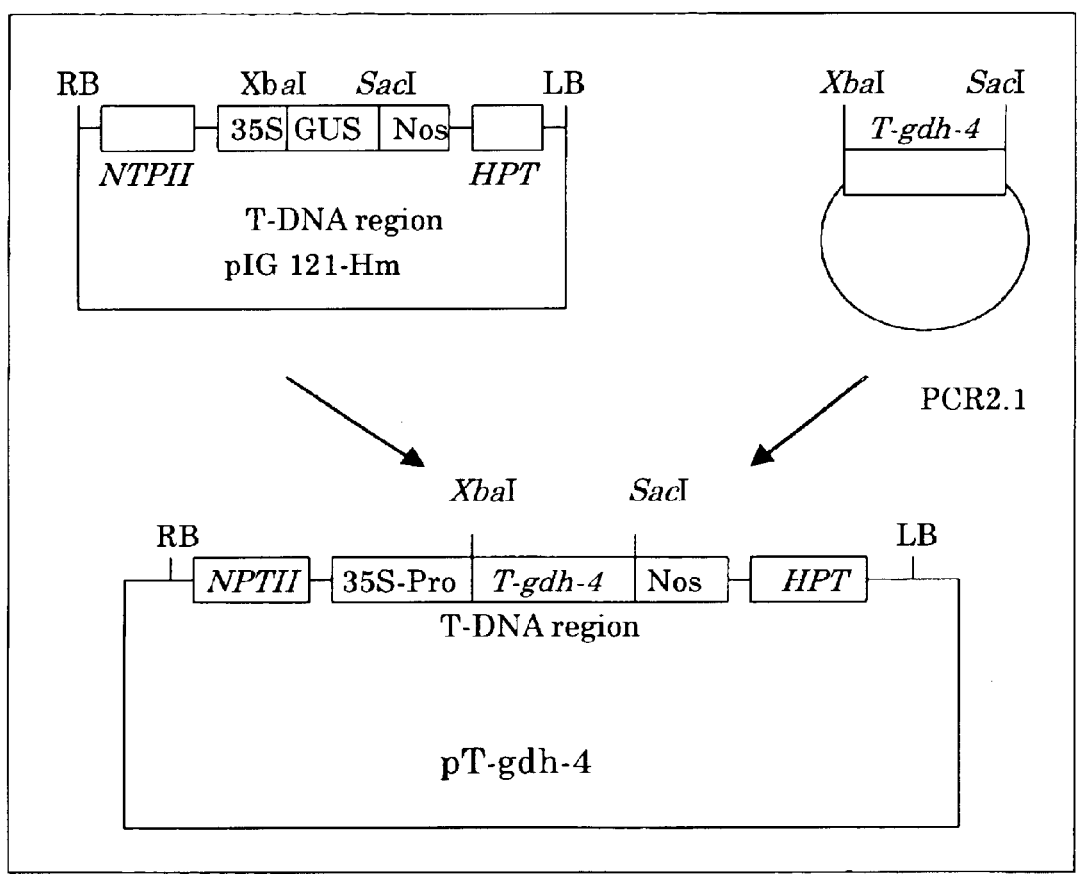
FIG. 9 shows a cloning process of tomato NAD-GDH gene (T-gdh-4) into Ti plasmid (pIG121-Hm).

Cloned tomato GDH gene (T-gdh-4) was introduced into Ti-plasmid (pIG121-Hm) to obtain plasmid pT-gdh-4. In the introduction, XbaI site and SacI site previously provided in the primer used in the isolation step were used. Ti plasmid containing T-gdh-4 gene (FIG. 9) was used to transform *Agrobacterium* strain EHA101. This strain was used for the infection of tomato.

(6) Subcloning of Tomato GDH Gene Variants into Ti Plasmid (pIG121-Hm)

Figure 10:
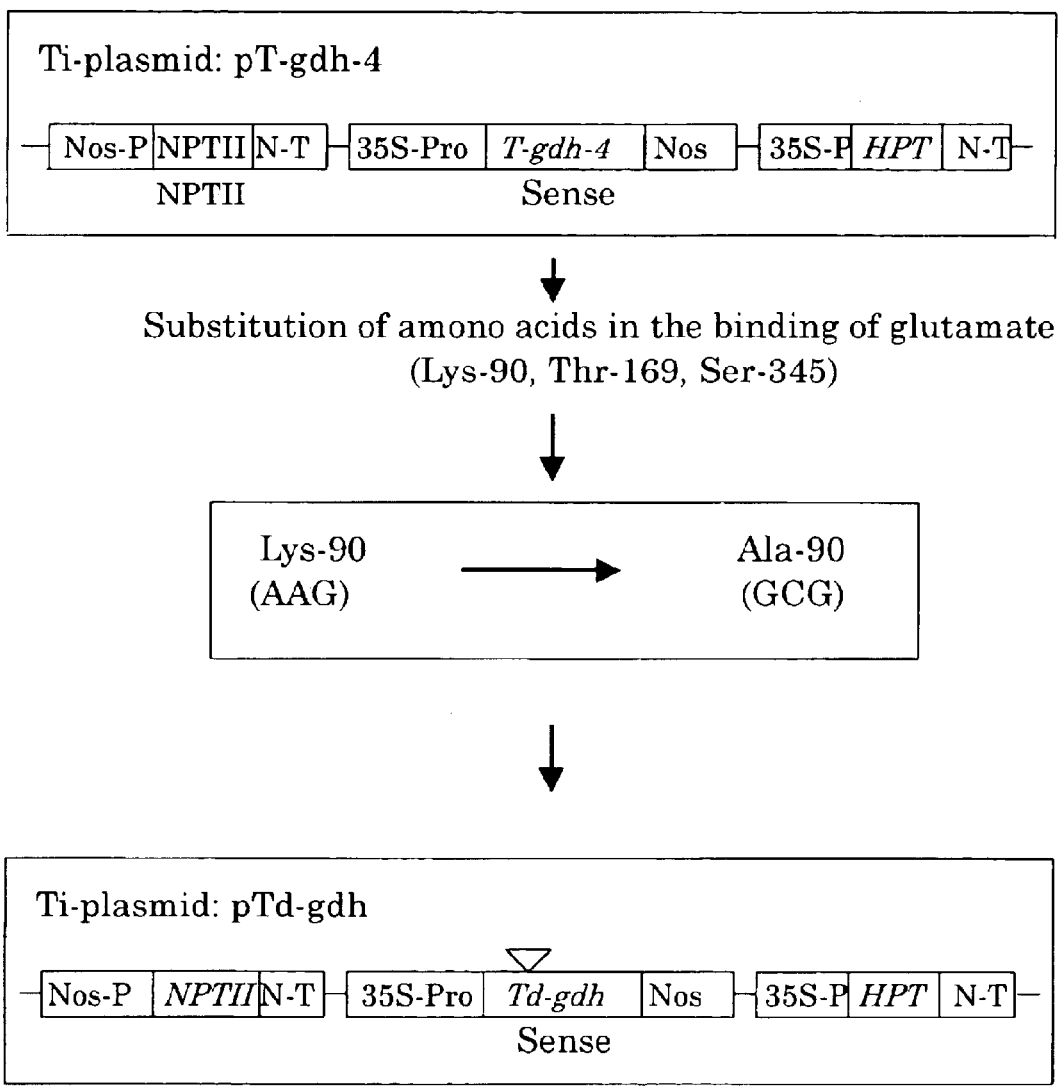
FIG. 10 is a rough sketch showing a process for modifying T-gdh-4 which is a tomato NAD-GDH gene.

Lysine at position 90 in tomato NAD-GDH which is the glutamic acid binding site was replaced with alanine, and the effect obtained by the replacement was examined (FIG. 10). This modification was conducted for the purpose of making the binding with ammonia impossible, because GDH gene of higher plants is inclined to reduce the amount of glutamic acid depending on ammonia ion concentration and nutrition conditions. The replacement of one amino acid was conducted by changing AAG encoding Lys with GCG encoding Ala by site-directed mutagenesis using PCR. The altered gene thus obtained was named "Td-gdh". Then Td-gdh gene sequence was introduced into Ti plasmid to obtain plasmid pTd-gdh (FIG. 10). The process is the same as that for T-gdh-4.

EXAMPLE 2

Production of Transformed Plant by the Infection of Tomato Cotyledons with *Agrobacterium*

Tomato (cultivar, minitomato) seeds were surface-sterilized with 70% ethanol (30 seconds) and 2% sodium hypochlorite (15 minutes), and then placed on a plant hormone-free MS agar medium. The seeds were cultured at 25° C. for one week while the daylight hours were kept to be 16 hours. The cotyledons were taken from the obtained sterile seedlings and then placed on an MS agar medium containing 2 mg/l of Zeatin and 0.1 mg/l of IAA (regeneration medium in 9 cm Petri dish), and cultured under the same conditions as those described above for 2 days. *Agrobacterium* (EHA 101) containing thus genetically constructed gene was cultured in YEP medium (Table 3) overnight and used for the infection. The cotyledons cultured for two days were collected in a sterilized Petri dish, and the *Agrobacterium* suspension was added to them to cause the infection. Superfluous *Agrobacterium* suspension was removed from the cotyledons by using a sterilized filter paper. After further removing superfluous *Agrobacterium* suspension, a sterilized filter paper was placed on the medium in the above-described Petri dish in order to prevent rapid propagation of *Agrobacterium*. The infected cotyledons were placed thereon and co-cultured for 24 hours.

The cotyledons were transferred into MS regeneration medium (selecting medium) containing 50 mg/l of kanamycin and 500 mg/l of Claforan to select the transformant. The regenerated shoots were transferred into a new selecting medium to conduct further selection. Well-grown green shoots were cut at the stems and transferred into a plant hormone-free MS medium (rooting medium in a test tube). The rooted, regenerated plant gradually got used to the soil.

TABLE 3

| Composition of YEP medium | (1 liter) |
|---|---|
| Bactotrypton | 10 g |
| Yeast extract | 10 g |
| glucose | 1 g |

EXAMPLE 3

Transformation of *Arabidopsis* by Vacuum Infiltration Method

The gene introduction into *Arabidopsis* was conducted by modified method of Bechtold N [C. R. Acad. Sci. Paris, Life Science 316; 1194–1199 (1993)]. *Arabidopsis* seeds were planted in a compost and cultivated at 22° C. for 10 days while the daylight hours were kept to be 16 hours. Each of the seedlings was planted in a rock wool (3 cm×3 cm), and the cultivation was continued under the same conditions for additional 3 weeks. When the plants began flower stalk formation, the top of each plant was pinched, and the cultivation was further continued for one week. *Agrobacterium* was cultured in YEP medium containing an antibiotic at 28° C. for 24 hours, and the microbes collected by the centrifugation (7,000 rpm, 10 minutes) were suspended in a suspension medium for infiltration (½ MS salt, ½ Gamborg B5 vitamin, 5% sucrose, 0.5 g/l MES, 0.044 μM benzylaminopurine, pH 5.7). After removing flowers and fruits which had been already formed, the plant was immersed in *Agrobacterium* suspension. They were placed in a desiccator and treated under reduced pressure (40 mmHg) for 15 minutes. The treated plant was cultivated for one month, and the seeds of them were taken. The seeds were planted in MS medium containing 50 mg/l of kanamycin and 200 mg/l of Claforan to select the transformed plant.

EXAMPLE 4

Production of Potato (May Queen) Transformant

Potatoes (May queen) were cut into pieces carefully so that sprouts would not be cut. The pieces were planted in a mixture of vermiculite and compost (1:1). About two weeks after, the apical meristem culture of the grown sprouts was conducted to obtain the sterile plants. The sterile plants were then placed on MS agar medium to increase the number of them. Then the microtubers were induced. At first, 100 ml Erlenmeyer flask was filled with 80 ml of MS liquid medium (MS medium, 2% sucrose, pH 5.7). Then three central nodes of the sterile plant were cut and transferred in the flask and the flask was shaking at 85 rpm at 25° C. at a well-lighted place to induce the rooting. Two weeks later, the rooted, well-growing plants were transferred into an MS liquid medium for microtuber induction (MS medium, 8% sucrose, pH 5.7, 40 ml medium in 100 ml Erlenmeyer flask), and the shaking culture was conducted at 80 rpm at 25° C. at a dark place. About one month after, the microtuber was cut into pieces of a thickness of about 2 mm. The pieces were transferred into an agar medium for regeneration (MS medium, 2% sucrose, 1 mg/l zeatin, 0.1 mg/l IAA, 1% agar). The pieces of the microtuber pre-cultured for two days were immersed in an *Agrobacterium* suspension obtained by the culture in an antibiotic-containing YEP medium for 24 hours. A filter paper was placed on the agar medium used as described above, the pieces were placed thereon and the co-culture was conducted for 48 hours. The culture product was transferred into a screening medium (MS medium, 2% sucrose, 1 mg/l zeatin, 1 mg/l IAA, 1% agar, 50 mg/l kanamycin, 500 mg/l Claforan). About two months after, the divided shoots were transferred into a rooting induction medium and then into a microtuber induction medium. The obtained microtubers were used for the analysis.

EXAMPLE 5

Confirmation of Introduced Gene

Figure 11:
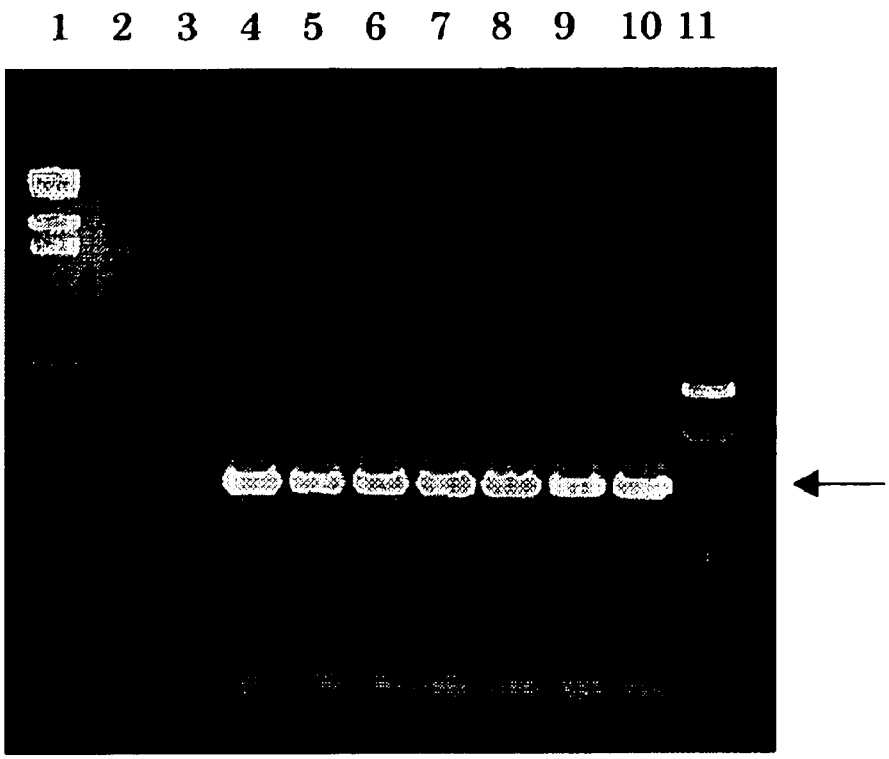
FIG. 11 shows a result of PCR analysis of a transformant obtained by introducing Aspergillus nidulans AN-gdh -17 gene, wherein:
lanes 2 and 3: untransformed tomatoes (Cont-1 and Cont-2)
lanes 4 to 6: transformed tomatoes (pMAT-1, pMAT-2 and pMAT-3) obtained by introducing plasmid (pMAT037) gene, and
lanes 7 to 10: transformed tomatoes (No. 6, No. 8-2, No. 15 and No. 17) obtained by introducing AN-gdh -17 gene.
Figure 12:
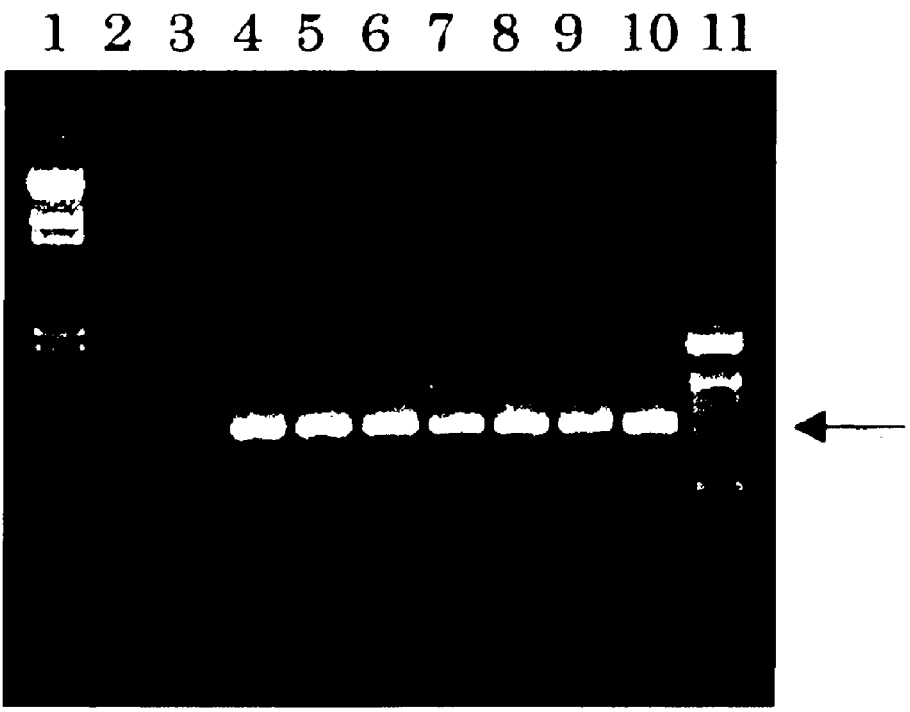
FIG. 12 shows a result of PCR analysis of a transformant obtained by introducing GDH (T-gdh-4) gene which is tomato NAD-GDH gene, wherein:
lanes 2 and 3: untransformed tomatoes
lanes 4 to 6: transformed tomatoes (pIG-1, pIG-2 and pIG-3) obtained by introducing plasmid (pIG121-Hm) gene
lanes 7 to 10: transformed tomatoes (No. 2, No. 7-2, No. 9–2 and No. 10) obtained by introducing T-gdh-4 gene.

Total DNA was extracted by method of Honda et al. [Honda and Hirai, Jpn. J. Breed 40, 339–348 (1990)] from 4 selected individuals obtained by the infection with *Agrobacterium* containing AN-gdh-17, 4 selected individuals obtained by the infection with *Agrobacterium* containing T-gdh-4 gene, 3 plant individuals obtained by the infection with *Agrobacterium* (only Ti plasmid) free of the intended gene, and 2 plant individuals obtained from the cotyledons by the direct regeneration without using *Agrobacterium*. DNA thus extracted was purified by RNAase treatment, phenol/chloroform treatment and PEG precipitation. The purified product was diluted to 0.01 µg/µl and used as a template for PCR. PCR reaction was conducted with primers 9 and 10 which amplify the region from Nos-Promoter to NPTII (PCR products, 1.0 kbp). The reaction conditions were as follows: 35 cycles under conditions of 94° C.—1 minute, 55° C.—1 minute and 72° C.—2 minutes. The PCR product was treated by the electrophoresis with 1% agarose gel and then dyed with ethidium bromide (FIGS. 11 and 12).

The primers used were as follows:

P9:   5'-CCCCTCGGTATCCAATTAGAG-3'   (SEQ ID:25)

P10:  5'-CGGGGGGTGGGCGAAGAACTCCAG-3'  (SEQ ID:26)

A band of an intended size was observed in four plant lines infected with AN-gdh-17 and four plant lines infected with T-gdh-4. From these results, it was confirmed that the gene had been introduced into four plant lines infected with Ti-plasmid containing AN-gdh-17 (FIG. 11) and four plant lines infected with Ti-plasmid containing T-gdh-4 gene (FIG. 12).

EXAMPLE 6

Confirmation of Expression of Introduced Gene

Figure 13:
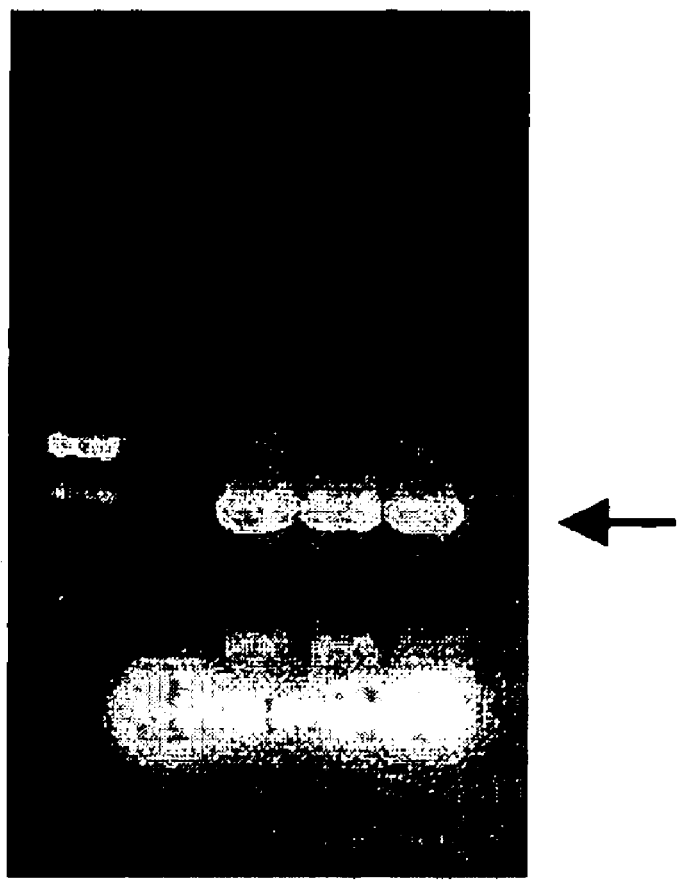
FIG. 13 shows a result of RT-PCR analysis of a transformant obtained by introducing Aspergillus nidulans AN-gdh-4 gene, wherein Nos. 6 and 15 each represent a transformed tomato, and tissues in parentheses are those from which whole RNA was extracted.
Figure 14:
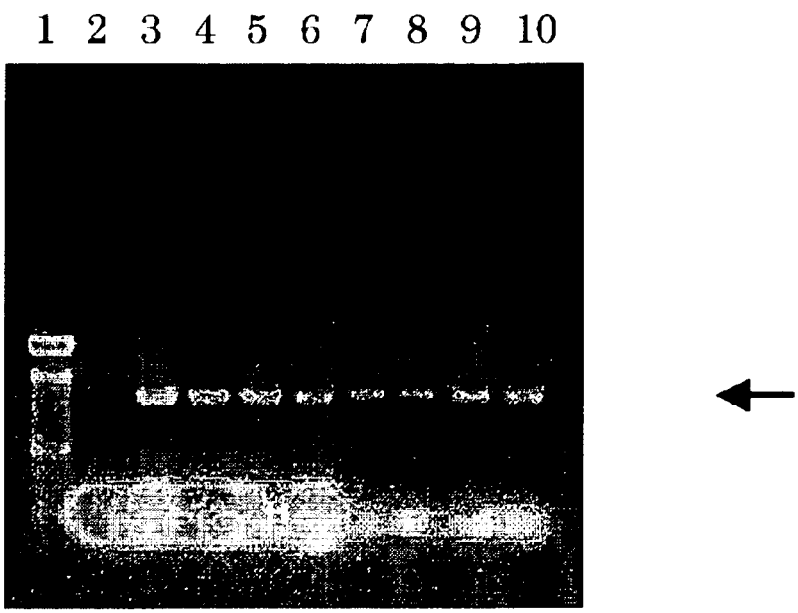
FIG. 14 shows a result of RT-PCR analysis of a transformant obtained by introducing tomato T-gdh-4 gene, wherein Nos. 2, 7-2, 9-2 and 10 each represent a transformed tomato, and tissues in parentheses are those from which whole RNA was extracted.

Then, the expression of the introduced gene was confirmed by RT-PCR by using transformed tomatoes in which the introduction of the intended gene had been confirmed. The total RNA was extracted from plant lines transfected with *Agrobacterium* containing AN-gdh-17 or T-gdh-4 gene and for which the genes introduction were confirmed in Example 5 and also from leaves and fruits of untransformed tomato, and the first strands cDNA were prepared. Then PCR was conducted with primers (SEQ ID:.3 and SEQ ID:4, and SEQ ID:5 and SEQ ID:6) used in the isolation of genes with the first-strand cDNA as the template. The reaction conditions were as follows: 30 cycles under conditions of 94° C.—1 minute, 55° C.—1 minute and 72° C.—2 minutes. As a result, the introduced gene confirmed to be expressed in all the leaves and fruits (FIGS. 13 and 14).

EXAMPLE 7

Extraction and Determination of Free Amino Acids

Fruits of the acclimated tomato transformant were harvested 6 weeks after the blossom, and stored at −80° C. Each fruit was cut into about 6 pieces, weighed, placed in a mortar, frozen with liquid nitrogen and ground. 3 ml of 80% ethanol was added thereto, and the obtained mixture was further thoroughly ground, transferred into a centrifugal tube and incubated at 80° C. for 20 minutes. After the centrifugation at 10,000 rpm for 20 minutes, the supernatant was transferred into another tube. 2 ml of 80% ethanol was added to the remaining pellets, and the pellets were ground again in the mortar and then incubated at 80° C. for 20 minutes. After the centrifugation, the supernatant was transferred into the tube containing the prior supernatant liquid to obtain a mixture. The total amount of the mixture was adjusted to 5 ml with 80% ethanol. After thorough mixing, 20 µl of the mixture was taken, dried and dissolved in 0.02 N hydrochloric acid. After the filtration through a 0.45 µm filter, a sample for the analysis was obtained. The amino acid analysis was conducted with Hitachi high-speed amino acid analyzer (L-8800).

Figure 15:
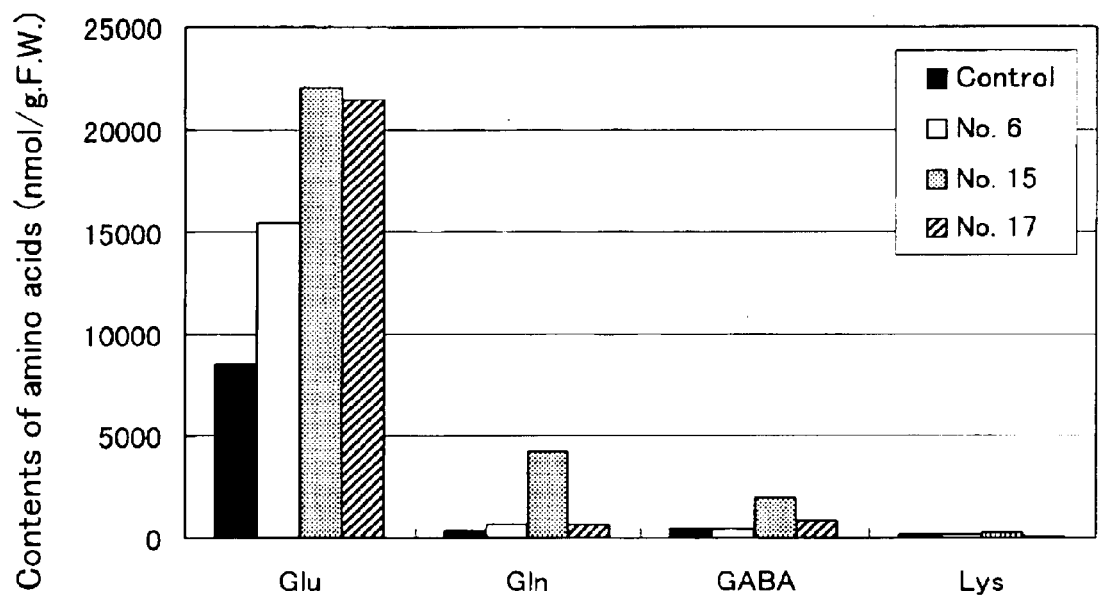
FIG. 15 is a graph showing the comparison of amino acid (glutamic acid—Glu, glutamine—Gln, γ-aminobutyric acid GABA and lysine—lys) content of transformants obtained by introducing AN-gdh-17 gene.

The amino acid analysis of the fruits (red) of a strain having AN-gdh-17 gene introduced therein was conducted 6 weeks after the bloom. The results of the analysis are shown in Table 4 together with the results of the analysis of untransformed plants (control plants). In the plant lines wherein glutamic acid content was remarkably increased, glutamic acid content was increased to 1.75 times (No. 6), 2.54 times (No. 15) and 2.48 times (No. 17) (FIG. 15). Amino acids other than glutamic acid, such as asparagine, aspartic acid, alanine, serine, threonine and histidine, were also increased in amount.

TABLE 4

Amino acid content of transformed tomato fruits into which
Aspergillus nidulans AN-gdh-17 gene was introduced

|  | Asp | Thr | Ser | Asn | Glu | Gln | Gly | Ala | Val | Met |
|---|---|---|---|---|---|---|---|---|---|---|
| Non-transgenic tomato |  |  |  |  |  |  |  |  |  |  |
| Control-1 | 1309 | 98 | 143 | 261 | 8876 | 680 | 22 | 295 | — | 15 |
| Control-2 | 1043 | 70 | 137 | 211 | 8482 | 394 | 20 | 221 | — | 19 |
| Plasmid (pMAT037) |  |  |  |  |  |  |  |  |  |  |
| pMAT-1 | 1326 | 139 | 316 | 232 | 6003 | 697 | 43 | 660 | 98 | 24 |
| pMAT-2 | 1998 | 195 | 371 | 227 | 11182 | 497 | 65 | 828 | — | 76 |
| pMAT-3 | 1280 | 217 | 439 | 368 | 3273 | 854 | 146 | 129 | 177 | 30 |
| Transgenic tomato (AN-gdh-17) |  |  |  |  |  |  |  |  |  |  |
| No. 6 | 1372 | 287 | 704 | 416 | 15162 | 649 | 149 | 1593 | 201 | 42 |
| No. 8-2 | 2660 | 178 | 508 | 271 | 13969 | 650 | 74 | 1187 | — | 19 |
| No. 15 | 5508 | 430 | 941 | 1180 | 22083 | 4289 | 160 | 2527 | 181 | 57 |
| No. 17 | 3187 | 239 | 691 | 384 | 21550 | 673 | 118 | 1749 | — | 38 |
|  | Ile | Leu | Tyr | Phe | GABA | Lys | His | Arg | Pro | Total |
| Non-transgenic tomato |  |  |  |  |  |  |  |  |  |  |
| Control-1 | 48 | 53 | 30 | 132 | 449 | 180 | 12 | 206 | 38 | 12774 |
| Control-2 | 22 | 41 | 16 | 76 | 447 | 196 | 129 | 45 | 40 | 11897 |
| Plasmid (pMAT037) |  |  |  |  |  |  |  |  |  |  |
| pMAT-1 | 63 | 46 | 25 | 154 | 135 | 88 | 172 | 84 | — | 10305 |
| pMAT-2 | 87 | 141 | 46 | 165 | 622 | 111 | 246 | 126 | — | 17091 |
| pMAT-3 | 165 | 138 | 228 | 291 | 222 | 116 | 246 | 78 | — | 12217 |
| Transgenic tomato (AN-gdh-17) |  |  |  |  |  |  |  |  |  |  |
| No. 6 | 220 | 234 | 58 | 378 | 458 | 188 | 388 | 209 | 119 | 22857 |
| No. 8-2 | 94 | 74 | 40 | 216 | 270 | 100 | 315 | 83 | 110 | 20818 |
| No. 15 | 225 | 220 | 163 | 391 | 1976 | 266 | 532 | 208 | 85 | 41422 |
| No. 17 | 123 | 129 | 61 | 275 | 817 | 136 | 374 | 153 | — | 30697 |

(nmol/g.F.W.)

Figure 16:
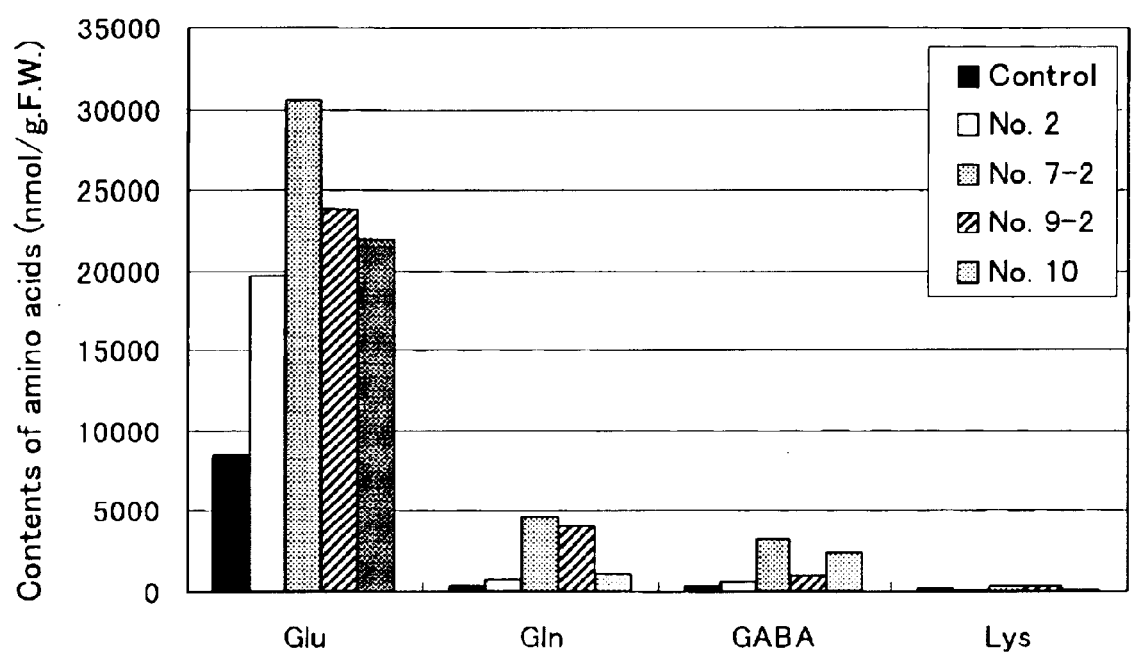
FIG. 16 shows the results of the comparison of amino acid (glutamic acid—Glu, glutamine—Gln, γ-aminobutyric acid GABA and lysine—lys) content of transformants obtained by introducing T-gdh-4 gene.

The amino acid analysis of the 4 strains containing tomato T-gdh-4 introduced therein was conducted by using the fruits taken 6 weeks after the blooming (Table 5). In the plant lines wherein the remarkable increase in glutamic acid content was observed, glutamic acid content was increased to 2.28 times (No. 2), 3.52 times (No. 7-2), 2.74 times (No. 9-2) and 2.53 times (No. 10) (FIG. 16). In the plant lines of a high glutamic acid content, amino acids other than glutamic acid, such as aspartic acid, asparagine, threonine, serine, alanine and histidine were also increased in amount. The total amino acid content was increased to 4 times (No. 7-2). The results are summarized in Table 5.

TABLE 5

Amino acid content of transformed tomato fruits into which
tomato GDH (T-gdh-4) gene was introduced

|  | Asp | Thr | Ser | Asn | Glu | Gln | Gly | Ala | Val | Met |
|---|---|---|---|---|---|---|---|---|---|---|
| Non-transgenic tomato |  |  |  |  |  |  |  |  |  |  |
| Control-1 | 1309 | 98 | 143 | 261 | 8876 | 680 | 22 | 295 | — | 15 |
| Control-2 | 1043 | 70 | 137 | 211 | 8482 | 394 | 20 | 221 | — | 19 |
| Plasmid (pIG121-Hm) |  |  |  |  |  |  |  |  |  |  |
| pIG-1 | 2133 | 203 | 371 | 357 | 9402 | 1072 | 73 | 1023 | 66 | 24 |
| pIG-2 | 1034 | 121 | 27 | 161 | 6588 | 298 | 70 | 677 | — | 14 |
| pIG-3 | 666 | 65 | 210 | 201 | 3637 | 153 | 25 | 349 | — | 20 |
| Transgenic tomato (T-gdh-4) |  |  |  |  |  |  |  |  |  |  |
| No. 2 | 4008 | 266 | 489 | 640 | 19755 | 749 | 82 | 1085 | — | 26 |
| No. 7-2 | 6205 | 553 | 555 | 91 | 30559 | 4711 | 77 | 803 | — | 49 |
| No. 9-2 | 4269 | 691 | 1152 | 1142 | 23810 | 3971 | 233 | 2247 | 270 | 116 |
| No. 10 | 6776 | 372 | 870 | 615 | 21955 | 1206 | 153 | 1825 | 99 | 44 |

TABLE 5-continued

Amino acid content of transformed tomato fruits into which tomato GDH (T-gdh-4) gene was introduced

|  | Ile | Leu | Tyr | Phe | GABA | Lys | His | Arg | Pro | Total |
|---|---|---|---|---|---|---|---|---|---|---|
| Non-transgenic tomato |  |  |  |  |  |  |  |  |  |  |
| Control-1 | 48 | 53 | 30 | 132 | 449 | 180 | 129 | 206 | 38 | 12774 |
| Control-Plasmid (pIG121-Hm) | 22 | 41 | 16 | 76 | 447 | 19 | 129 | 45 | 40 | 11897 |
| pIG-1 | 92 | 93 | 58 | 237 | 330 | 173 | 263 | 113 | — | 16083 |
| pIG-2 | 60 | 70 | 83 | 105 | 232 | 96 | 146 | 70 | — | 10095 |
| pIG-3 | 15 | 20 | — | 102 | 135 | 32 | 255 | — | — | 5885 |
| Transgenic tomato (T-gdh-4) |  |  |  |  |  |  |  |  |  |  |
| No. 2 | 127 | 139 | 65 | 223 | 594 | 172 | 371 | 137 | — | 28928 |
| No. 7-2 | 223 | 192 | 179 | 464 | 3195 | 333 | 743 | 311 | 111 | 50153 |
| No. 9-2 | 478 | 506 | 163 | 587 | 1039 | 406 | 695 | 394 | 305 | 42169 |
| No. 10 | 209 | 202 | 136 | 431 | 2412 | 192 | 627 | 176 | — | 38030 |

(nmol/g.F.W.)

EXAMPLE 8

Analysis of Subsequent Generation ($T_1$) of Tomato Transformant

1) Selection of $T_1$ Generation

Seeds of transformed tomato ($T_0$ generation) obtained by introducing a gene by *Agrobacterium* method were surface-sterilized with 80% ethanol for 30 seconds and 2% sodium hypochlorite for 15 minutes, and then planted in MS agar medium containing 350 mg/l of kanamycin under sterile conditions. One month later, well-grown plants were selected and made to acclimated to the soil. The plants were cultured in an outdoor closed system greenhouse in order to increase the number of fruits per plant. To make the nutrition conditions uniform, no additional fertilizer was given after the transplantation into 1 kg of culture soil (Power soil; Sakata no Tane) during the acclimation to the soil. In the following analysis, leaves were not picked in order to uniform the assimilation, and the lateral buds were cultivated under uniform conditions. The tissues of the leaves thus obtained were used.

Seeds of the transformant of the subsequent generation ($T_1$) were selected on an agar medium containing 350 mg/l of kanamycin, an antibiotic, under sterile conditions. As a result, selected plants were obtained from No. 1, No. 3, No. 15 and No. 2.1 in transgenic lines, and also from No. 1, No. 3 and No. 8 in T-gdh-4 gene-introduced plant lines.

2) Confirmation of Introduced Gene by Southern Analysis

Total DNA was extracted from leaf tissues of lateral buds of the acclimated plant [Honda and Hirai, Jan. J. Breed 40, 339–348 (1990)]. 15 μg of DNA was treated with the combination of restriction enzymes BamHI and EcoRI and also reacted with XbaI. After the electrophoresis, it was transferred on a nylon membrane. The obtained product was then subjected to Southern hybridization with a DIG-Labeling and Detection Kit (Roche Molecular Biochemicals). AN-gdh-17 gene or T-gdh-4 gene was used as the probe.

Figure 17:
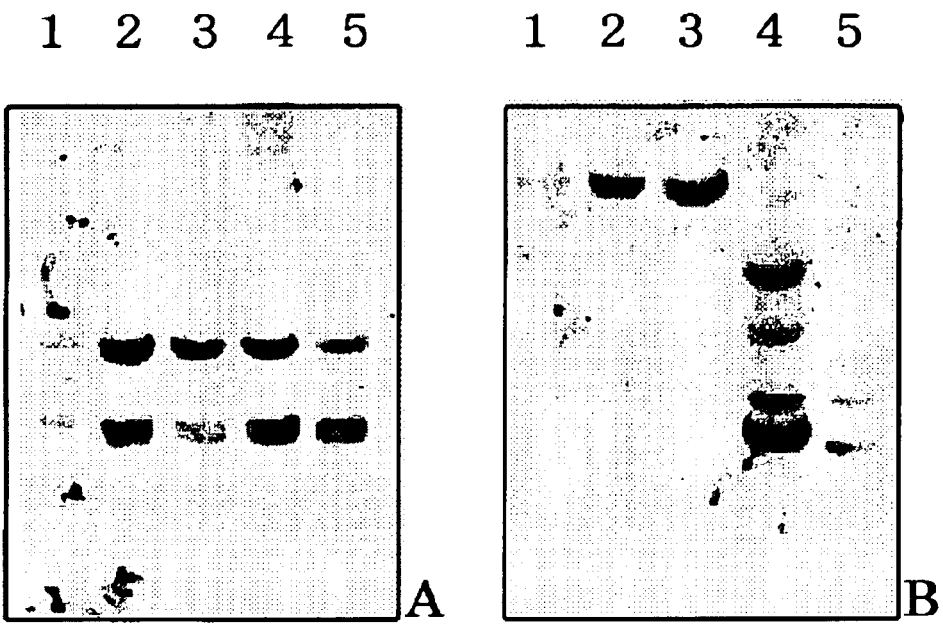
FIG. 17 shows the result of Southern analysis of transgenic tomato ($T_1$) with AN-gdh-17 gene of Aspergillus nidulans. Specifically.
Figure 18:
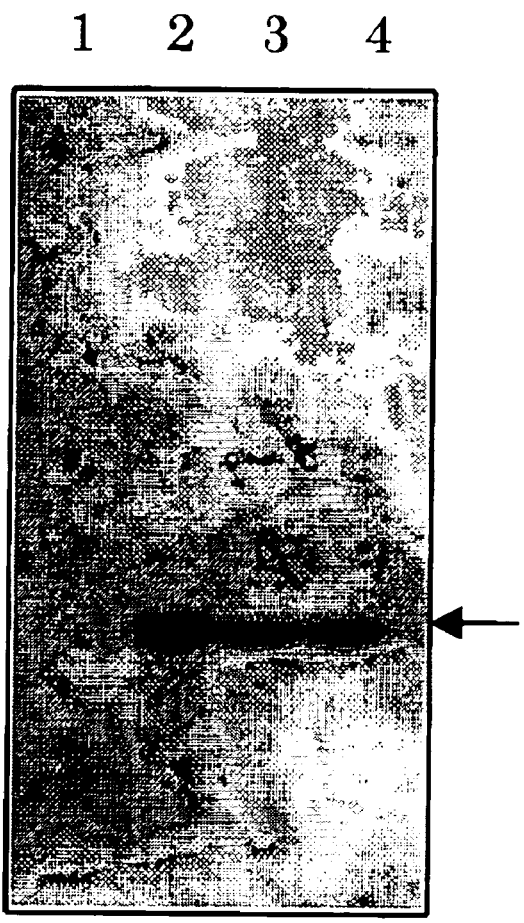
FIG. 18 shows the result of Southern analysis of transgenic tomato with T-gdh-4 gene of tomato.

Southern hybridization conducted with AN-gdh-17 gene as the probe confirmed that the gene was introduced into No. 1, No. 3, No. 15 and No. 2.1 in transgenic lines (FIG. 17). In the same manner, Southern hybridization was conducted with T-gdh-4 gene as the probe. A band (1.4 kbp) of a size equal to that of T-gdh-4 gene was confirmed (FIG. 18).

3) Determination of Activity of NADP-GDH and NAD-GDH

Leaf tissue (0.2 g) of lateral buds of transformed tomato ($T_1$) was frozen with liquid nitrogen, and then crushed in a mortar. 5 parts by weight of an extract buffer [200 mM Tris (pH 8.0), 14 mM β-mercaptoethanol, 10 mM L-cysteine-HCl, 0.5 mM PMSF, 0.5% Triton X-100] was added to 1 part by weight of the obtained powder. The obtained mixture was transferred into a centrifugal tube and centrifuged at 12,000 rpm at 4° C. for 10 minutes. The supernatant was ultrafiltrated (Millipore, ultrafree 0.5 filter unit, Biomax-10) and washed with the extract buffer three times.

The extracted enzyme was mixed with a reaction mixture [100 mM Tris (pH 8.0), 20 mM 2-α-ketoglutarate, 1.0 mM $CaCl_2$,, 0.2 mM NADPH (NADP-GDH activity determination) or 0.2 mM NADH (NAD-GDH activity determination), 200 mM ammonium chloride], and the reaction was carried out at room temperature. The reduction in the absorbance at 340 nm was determined.

NADP-GDH activity was determined by using leaf tissue of transformed tomato ($T_1$) containing AN-gdh-17 gene introduced therein. The activity of the transformant could be determined to be 120 to 500 nmol/min.mg protein, while no activity of the untransformed product was recognized (Table 6). NAD-GDH activity of the plant line containing T-gdh-4 gene introduced therein was increased to about 1.6 times as high as that of the untransformed product (Table 7).

TABLE 6

NADP-GDH activity of transgenic tomato with AN-gdh-17 gene of *Aspergillus nidulans*.

| Lines | Activity of NADP-GDH (nmol/min · mg protein) |
|---|---|
| Non-transgenic tomato | 0 |
| Transgenic tomato |  |
| AN-gdh-17 No. 1-1 | 400 |
| AN-gdh-17 No. 3-1 | 390 |
| AN-gdh-17 No. 15-1 | 380 |
| AN-gdh-17 No. 2.1-1 | 230 |

TABLE 7

NAD-GDH activity of transgenic tomato with T-gdh-4 gene of tomato

| Lines | Activity of NAD-GDH (nmol/min · mg protein) |
|---|---|
| Non-transgenic tomato | 80 |
| Transgenic tomato | |
| T-gdh No. 1-2 | 180 |
| T-gdh No. 3-1 | 160 |
| T-gdh No. 8-1 | 260 |

4) Determination of Amino Acid Content of Fruits

Three fruits taken in the $6^{th}$ week after blossoming of the first fruit cluster were used for the analysis. 3 parts by weight of 80% ethanol heated to 80° C. was added to 1 part by weight of the fruits. The obtained mixture was ground in a mortar and then heated again to 80° C. for 20 minutes. After the centrifugation at 7,000 rpm, the obtained supernatant liquid was recovered. After the addition of 80% ethanol, the obtained mixture was heated to 80° C. The extraction with ethanol was conducted three times, and the obtained extracts were combined together and then 80% ethanol was added thereto to make the total amount 100 ml. After thoroughly mixing, 200 µl of the extract was taken in an Eppendrof tube, dried and then dissolved in 200 µl of sterilized water. 200 µl of ethyl ether was added to the obtained solution, and they were mixed together and then centrifuged at 12,000 rpm. The ether layer was removed. The aqueous layer was dried again and dissolved in 200 µl of 0.02 N HCl. The resultant solution was filtered through a 45 µm filter, and the filtrate was taken as a sample and analyzed with Hitachi high-speed amino acid analyzer (L-8800).

Figure 19:
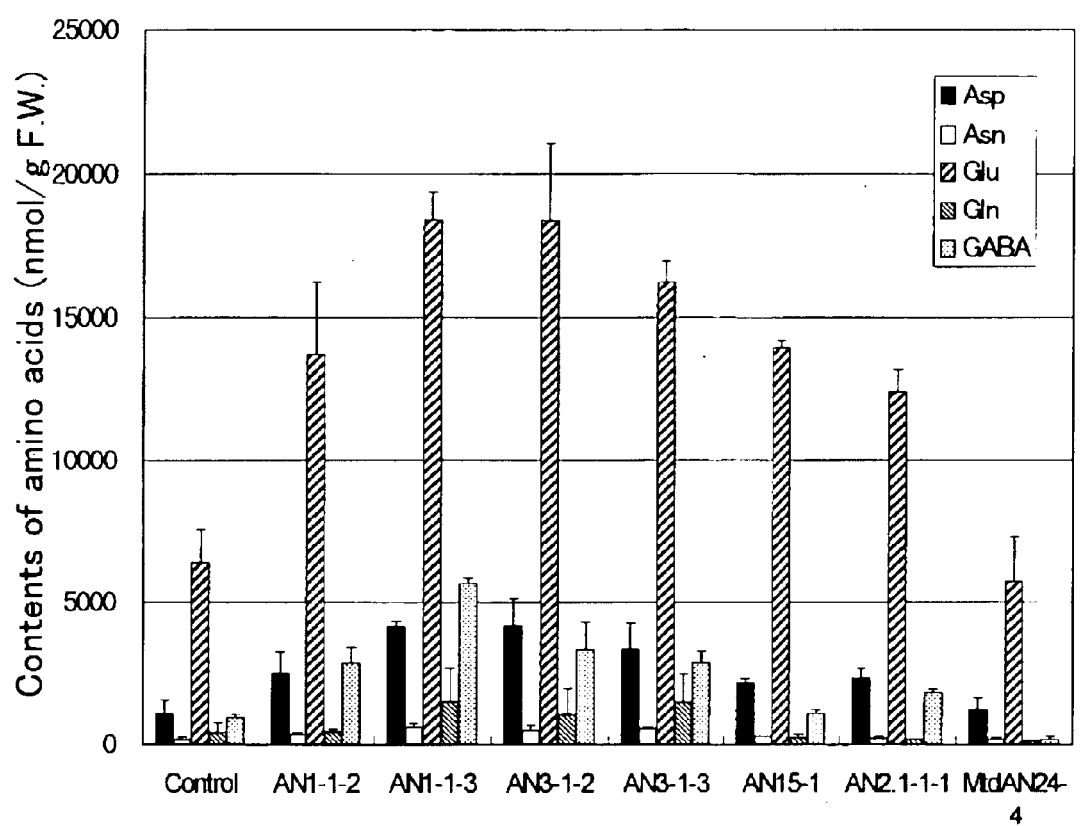
FIG. 19 shows amino acids contens in fruits of $T_1$ tomato transformed with AN-gdh-17 gene of Aspergillus nidulans.

Amino acid content of three fruits of the first fruit cluster of transformed tomatoes was determined 6 weeks after the blossoming. The results were shown by the average of the three fruits. Glutamic acid contents of AN 1-1-2 and AN 1-1-3 from AN-gdh-17 No. 1 plant line were increased to 2.1 times and 2.8 times as high as that of the untransformed fruit, respectively. Also, glutamic acid contents of AN 3-1-2 and AN 3-1-3 from AN-gdh-17 No. 3 plant line were increased to 2.8 times and 2.5 times as high as that of the untransformed fruit. Further, glutamic acid contents of AN 15-1 from AN-gdh-17 No. 15 plant line and AN2.1-1-1 from AN-gdh-17 No. 2.1 plant line were also increased to 2.1 times and 1.9 times, respectively (Table 8, FIG. 19). The similar tendency was observed also in the subsequent generation of No. 15 plant line which had had a high glutamic acid content in the transformed generation ($T_0$). In a plant line containing Mt-dAN-gdh gene, i.e. MtdAN-24-4, no significant difference in glutamic acid content from the untransformed fruit was recognized.

TABLE 8

Amino acid contents in fruits of $T_1$ tomato transformed with AN-gdh-17 gene of *Aspergillus nidulans* . . .

| | Asp | Thr | Ser | Asn | Glu | Gln | Gly | Ala | Val | Met |
|---|---|---|---|---|---|---|---|---|---|---|
| Control | 1093 | 100 | 220 | 184 | 6416 | 443 | 14 | 287 | 85 | 19 |
| | (484)[a] | (33) | (51) | (91) | (1156) | (331) | (8) | (111) | (54) | (9) |
| AN 1-1-2 | 2495 | 188 | 414 | 381 | 13709 | 453 | 39 | 615 | 176 | 43 |
| | (781) | (19) | (17) | (44) | (2549) | (111) | (8) | (158) | (20) | (3) |
| AN 1-1-3 | 4168 | 416 | 861 | 628 | 18420 | 1501 | 107 | 1540 | 167 | 49 |
| | (154) | (63) | (87) | (130) | (993) | (1203) | (22) | (150) | (13) | (10) |
| AN 3-1-2 | 4180 | 304 | 655 | 499 | 18387 | 1046 | 88 | 1253 | 154 | 44 |
| | (962) | (69) | (189) | (180) | (2736) | (909) | (64) | (844) | (43) | (11) |
| AN 3-1-3 | 3368 | 332 | 706 | 569 | 16253 | 1492 | 73 | 1183 | 143 | 38 |
| | (888) | (52) | (122) | (65) | (730) | (1016) | (37) | (475) | (6) | (6) |
| AN 15-1 | 2179 | 153 | 359 | 289 | 13949 | 267 | 21 | 725 | 191 | 29 |
| | (157) | (19) | (20) | (7) | (280) | (97) | (30) | (133) | (84) | (1) |
| AN 2.1-1-1 | 2325 | 203 | 460 | 233 | 12426 | 187 | 38 | 914 | 132 | 28 |
| | (378) | (38) | (168) | (57) | (774) | (28) | (24) | (465) | (38) | (7) |
| MtdAN 24-4 | 1233 | 129 | 320 | 183 | 5751 | 116 | 28 | 547 | 124 | 22 |
| | (415) | (37) | (74) | (77) | (1584) | (42) | (12) | (186) | (10) | (4) |

| | Ile | Leu | Tyr | Phe | GABA | Lys | His | Arg | Pro | Total |
|---|---|---|---|---|---|---|---|---|---|---|
| Control | 38 | 42 | 47 | 87 | 961 | 43 | 127 | 118 | 37 | 10363 |
| | (18) | (9) | (5) | (36) | (108) | (16) | (41) | (167) | (42) | (4235) |
| AN 1-1-2 | 111 | 118 | 60 | 142 | 2860 | 101 | 234 | 41 | 0 | 22179 |
| | (23) | (14) | (7) | (32) | (575) | (35) | (15) | (70) | (0) | (3713) |
| AN 1-1-3 | 223 | 199 | 124 | 515 | 5672 | 233 | 435 | 75 | 130 | 35464 |
| | (46) | (21) | (23) | (96) | (183) | (36) | (17) | (130) | (28) | (2882) |
| AN 3-1-2 | 203 | 211 | 101 | 483 | 3334 | 203 | 391 | 72 | 148 | 31755 |
| | (104) | (121) | (21) | (105) | (967) | (39) | (78) | (125) | (164) | (4759) |
| AN 3-1-3 | 190 | 185 | 112 | 491 | 2902 | 180 | 386 | 76 | 0 | 28677 |
| | (73) | (86) | (17) | (91) | (403) | (42) | (55) | (107) | (0) | (1217) |
| AN 15-1 | 90 | 86 | 49 | 101 | 1086 | 101 | 230 | 0 | 65 | 19970 |
| | (16) | (16) | (14) | (12) | (131) | (36) | (97) | (0) | (91) | (253) |
| AN 2.1-1-1 | 105 | 100 | 51 | 153 | 1842 | 90 | 242 | 0 | 60 | 19589 |
| | (56) | (40) | (8) | (64) | (93) | (36) | (97) | (0) | (85) | (2287) |
| MtdAN 24-4 | 74 | 53 | 52 | 96 | 187 | 52 | 228 | 0 | 0 | 9195 |
| | (21) | (18) | (8) | (34) | (103) | (17) | (5) | (0) | (0) | (2644) |

[a]Values in parentheses are standard error (n = 3). (nmol/gF.W.)

Figure 20:
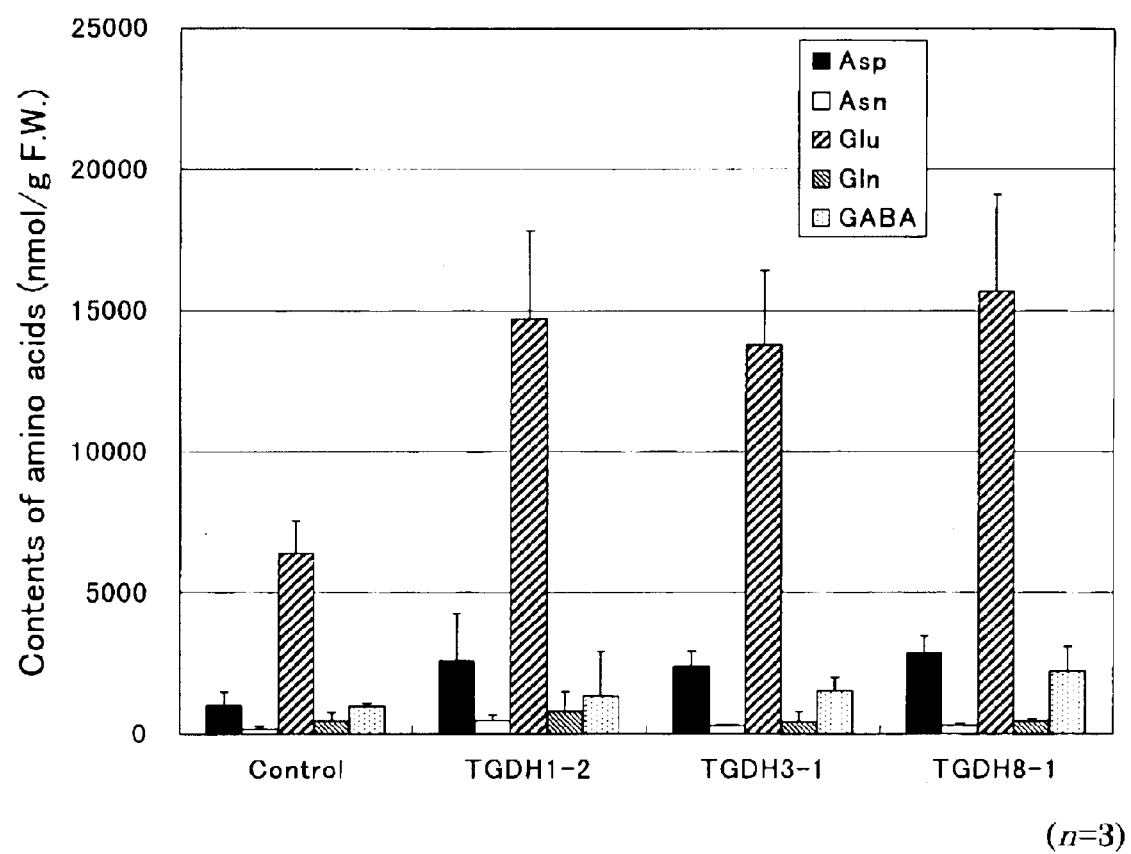
FIG. 20 shows amino acids contents in fruits of $T_1$ tomato transformed with T-gdh-4 gene of tomato.

In plant lines containing T-gdh-4 gene introduced therein, glutamic acid content of TGDH 1-2, 3-1 and 8-1, which were the subsequent generations of examined T-gdh-4, Nos. 1, 3 and 8 plant lines, were increased to 2.3 times, 2.1 times and 2.4 times, respectively, as high as that of the untransformed fruit (Table 9, FIG. 20). As for amino acids other than glutamic acid, a remarkable increase in asparatic acid content, glutamine content and GABA content was observed. As a result, the total free amino acid content was also increased to twice as high as that of the untransformed plant.

(1990)]. 15 μg of DNA was treated with restriction enzyme EcoRI. After the electrophoresis, it was transferred on a nylon membrane. The obtained product was then subjected to Southern hybridization with a DIG-Labeling and Detection Kit (Roche Molecular Biochemicals). AN-gdh-17 gene was used as the probe.

After the infection with *Agrobacterium* having Ti plasmid, pMt-dAN-gdh and pCt-AN-gdh, the screening was conducted on a medium containing 50 mg/l of kanamycin. Four plant lines, i. e. Mt-dAN-gdh Nos. 2, 5 and 8 and Ct-AN-gdh No. 1, could be selected. Southern hybridization

TABLE 9

Amino acids contents in fruits of T1 tomato transformed with T-gdh-4 gene of tomato.

|  | Asp | Thr | Ser | Asn | Glu | Gln | Gly | Ala | Val | Met |
|---|---|---|---|---|---|---|---|---|---|---|
| Control | 1093 | 100 | 220 | 184 | 6416 | 443 | 14 | 287 | 85 | 19 |
|  | (484)[a] | (33) | (51) | (91) | (1156) | (331) | (8) | (111) | (54) | (9) |
| T-gdh 1-2 | 2610 | 279 | 559 | 480 | 14737 | 788 | 51 | 905 | 156 | 32 |
|  | (506) | (51) | (119) | (19) | (3122) | (647) | (28) | (563) | (45) | (4) |
| T-gdh 3-1 | 2414 | 201 | 440 | 302 | 13810 | 428 | 57 | 697 | 155 | 32 |
|  | (505) | (36) | (127) | (6) | (2639) | (367) | (20) | (347) | (55) | (12) |
| T-gdh 8-1 | 2846 | 216 | 460 | 309 | 15699 | 464 | 38 | 694 | 120 | 30 |
|  | (596) | (50) | (112) | (69) | (3465) | (67) | (4) | (53) | (5) | (3) |

|  | Ile | Leu | Tyr | Phe | GABA | Lys | His | Arg | Pro | Total |
|---|---|---|---|---|---|---|---|---|---|---|
| Control | 38 | 42 | 47 | 87 | 961 | 43 | 127 | 118 | 37 | 10363 |
|  | (18) | (9) | (5) | (36) | (108) | (16) | (41) | (167) | (42) | (4235) |
| T-gdh 1-2 | 100 | 123 | 117 | 252 | 1312 | 295 | 293 | 158 | 45 | 23291 |
|  | (27) | (45) | (19) | (139) | (958) | (257) | (165) | (194) | (58) | (3883) |
| T-gdh 3-1 | 112 | 110 | 66 | 203 | 1525 | 122 | 273 | 69 | 73 | 21089 |
|  | (34) | (38) | (8) | (19) | (478) | (8) | (59) | (98) | (103) | (2800) |
| T-gdh 8-1 | 100 | 101 | 64 | 313 | 2236 | 132 | 233 | 35 | 128 | 24217 |
|  | (15) | (18) | (6) | (45) | (846) | (31) | (183) | (60) | (33) | (5189) |

[a]Values in parentheses are standard error (n = 3). (nmol/g.F.W.)

EXAMPLE 9

Production and Analysis of Transgenic Potatoes

1) Production of Transformants (Refer to Example 4)

Sterile potatoes were obtained by shoot apex culture. The materials were propagated by shoot apex subculture. A shoot apex was placed in a liquid culture medium (10 ml) prepared by adding 2% sucrose to MS medium to induce the rooting. After completion of the rooting, 10 ml of MS liquid medium containing 16% sucrose was added to the medium, and dark culture was conducted to induce the formation of microtubers. The 6 to 8 week old microtubers were cut to form disc-shaped pieces. After peeling, the pieces were infected with an *Agrobacterium* suspension (Ti-plasmid. pMt-dAN-gdh or pCt-AN-gdh) cultured at 28° C. overnight. A sterilized filter paper was placed on MS agar medium (MS medium, 2.0 mg/l Zeatin, 0.1 mg/l indole acetic acid, 0.3% gelrite), the pieces were placed thereon and co-cultured at 25° C. for 2 days while the daylight hours were kept to be 16 hours. The culture was then transferred to a screening medium (MS medium, 2.0 mg/l Zeatin, 0.1 ml/l indole acetic acid, 0.3% gelrite, 50 mg/l kanamycin and 500 mg/l claforan) and cultured under the same conditions as those described above. The cultures were transferred into the fresh screening medium every week, and the differentiated shoots were transferred into a plant hormone-free screening medium to induce the rooting.

Figure 21:
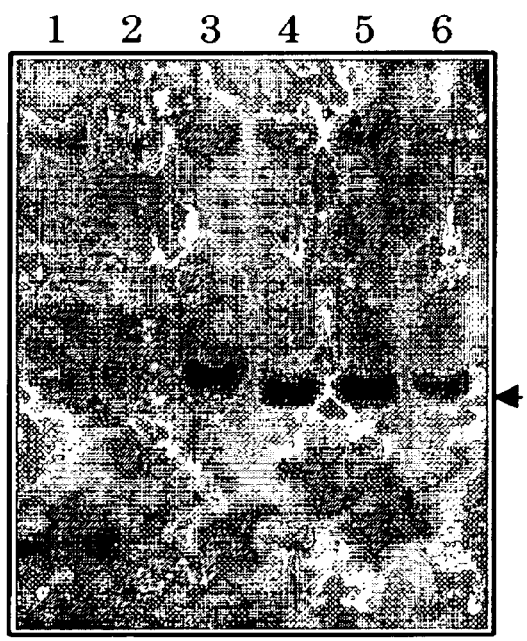
FIG. 21 shows a Southern analysis of transgenic potato with Ct-AN-gdh and Mt-dAN-gdh gene of Aspergillus nidulans.

2) Confirmation of Introduced Gene by Southern Analysis: Tolal DNA was extracted from leaf tissues of the acclimated plant [Honda and Hirai, Jan. J. Breed 40, 339–348 (1990)]. was conducted with AN-gdh-17 gene as the probe. A band of the intended size was confirmed (FIG. 21) to suggest that gdh gene added with transit peptide was introduced therein.

3) Determination of Activity of NADP-GDH

Leaf tissue (about 0.1 g) of transformed tomato was frozen with liquid nitrogen, and then crushed in a mortar. 5 parts by weight of an extract buffer [200 mM Tris (pH 8.0), 14 mM β-mercaptoethanol, 10 mM L-cysteine-HCl, 0.5 mM PMSF, 0.5% Triton X-100] was added to 1 part by weight of the obtained powder. The obtained mixture was transferred into a centrifugal tube and centrifuged at 12,000 rpm for 10 minutes. The supernatant was ultrafiltrated (Millipore, ultrafree 0.5 filter unit, Biomax-10) and washed with the extract buffer three times.

The extracted enzyme was mixed with a reaction liquid [100 mM Tris (pH 8.0), 20 mM 2-α-ketoglutarate, 1.0 mM $CaCl_2$,, 0.2 mM NADPH, 200 mM ammonium chloride], and the reaction was carried out at room temperature. The reduction in the absorbance at 340 nm was determined.

NADP-GDH activity was determined by using leaf tissue of transformed potato in which the introduced gene could be confirmed by Southern analysis. As a result, the activity of the transformant could be determined to be 154 to 300 nmol/min.mg protein, while no activity of the untransformed product was recognized (Table 10). Mt-dAN-gdh plant line showed higher activity than Ct-AN-gdh plant line.

TABLE 10

NADP-GDH activity of transgenic potato with Mt-dAN-gdh and Ct-AN-gdh gene of *Aspergillus nidulans*

| Lines | Activity of NADP-GDH (nmol/min · mg protein) |
|---|---|
| Non-transgenic potato | 0 |
| Transgenic potato | |
| Mt-dAN-gdh No. 2 | 290 |
| Mt-dAN-gdh No. 5 | 300 |
| Mt-dAN-gdh No. 8 | 260 |
| Ct-AN-gdh No. 1 | 150 |

4) Determination of Amino Acid Content of Microtubers

The shoot apexes of 4 plant lines (both untransformed and transformed) were liquid-cultured to induce the rooting, and then 16% sucrose was added to the culture medium. 6 weeks after the treatment in a dark place, amino acid content of the microtubers was determined.

3 parts by weight of 80% ethanol heated to 80° C. was added to 1 part by weight of the specimens. The obtained mixture was ground in a mortar and then heated again to 80° C. for 20 minutes. After the centrifugation at 7,000 rpm and the obtained supernatant was recovered. After the addition of 80% ethanol, the obtained mixture was heated to 80° C. The extraction with ethanol was conducted three times, and the obtained extracts were combined together and then 80% ethanol was added thereto to make the total amount of 5 ml. After thoroughly mixing, 200 µl of the extract was taken in an Eppendrof tube, dried and then dissolved in 200 µl of sterilized water. 200 µl of ethyl ether was added to the obtained solution, and they were mixed together and then centrifuged at 12,000 rpm. The ether layer was removed. The aqueous layer was dried again and dissolved in 400 µl of 0.02 N HCl. The resultant solution was filtered through a 0.45 µm filter, and the filtrate was taken as a sample and analyzed with Hitachi high-speed amino acid analyzer (L-8800).

Figure 22:
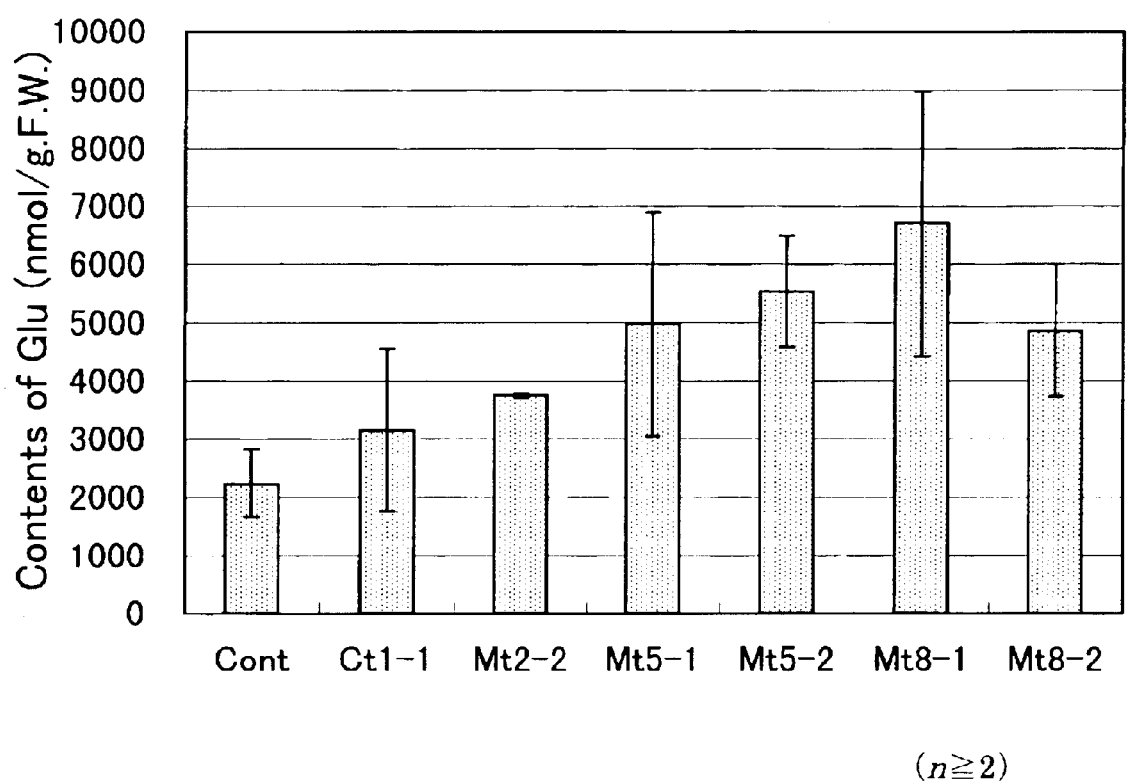
FIG. 22 shows the contents of Glu in microtuber of potato transformed with Ct-AN-gdh and Mt-dAN-gdh gene.

Amino acid analysis of microtubers derived from the plant lines containing gene introduced therein was conducted. At least two microtubers were analyzed for each lnes, and the analytical results were statistically treated. Glutamic acid contents of Mt 2—2, Mt 5-1, Mt 5-2, Mt 8-1 and Mt 8-2 lines from No 2, 5 and 8 plant lines containing Mt-dAN-gdh gene introduced therein were increased to 1.7 times, 2.2 times, 2.5 times, 3.0 times and 2.2 times as high as that of the untransformed sample, respectively (Table 11, FIG. 22). In a plant line containing Ct-AN-gdh gene, no significant difference in glutamic acid content from the untransformed sample was recognized. As for amino acids other than glutatamic acid, a remarkable increase in glutamine content and proline content was observed. Consquently, the total free amino acid content was also increased to 2 to 3 times as high as that of the untransformed plant.

TABLE 11

Amino acid contents in microtuber of potato transformed with Ct-AN-gdh and Mt-dAN-gdh gene of *Aspergillus nidulans*

| | Asp | Thr | Ser | Asn | Glu | Gln | Gly | Ala | Val | Met |
|---|---|---|---|---|---|---|---|---|---|---|
| Control | 1079 | 475 | 664 | 13771 | 2248 | 9995 | 181 | 518 | 1726 | 257 |
| | (234)[a] | (132) | (248) | (6238) | (577) | (4252) | (57) | (297) | (301) | (80) |
| Ct-AN no. 1-1 | 1473 | 786 | 1573 | 42117 | 3162 | 17744 | 465 | 1423 | 2197 | 289 |
| | (357) | (215) | (214) | (17048) | (1399) | (5291) | (217) | (594) | (1110) | (185) |
| Mt-dAN no. 2-2 | 1845 | 880 | 1310 | 14789 | 3752 | 27480 | 407 | 1665 | 3536 | 456 |
| | (3) | (15) | (33) | (2396) | (32) | (1979) | (9) | (29) | (90) | (7) |
| Mt-dAN no. 5-1 | 1623 | 843 | 1323 | 11120 | 4979 | 34087 | 465 | 1141 | 2373 | 497 |
| | (34) | (294) | (536) | (2545) | (1927) | (8110) | (159) | (506) | (240) | (137) |
| no. 5-2 | 4167 | 742 | 1444 | 28624 | 5544 | 25310 | 311 | 1857 | 2149 | 286 |
| | (3012) | (87) | (17) | (3280) | (948) | (3195) | (11) | (174) | (694) | (103) |
| Mt-dAN no. 8-1 | 2316 | 884 | 1566 | 30968 | 6712 | 20073 | 495 | 1892 | 2288 | 209 |
| | (607) | (186) | (244) | (2156) | (2277) | (4897) | (149) | (249) | (539) | (85) |
| no. 8-2 | 2001 | 829 | 1119 | 16692 | 4863 | 14561 | 365 | 1057 | 2427 | 320 |
| | (277) | (154) | (127) | (2796) | (1135) | (2926) | (50) | (193) | (1244) | (143) |

| | Ile | Leu | Tyr | Phe | GABA | Lys | His | Arg | Pro | Total |
|---|---|---|---|---|---|---|---|---|---|---|
| Control | 177 | 126 | 46 | 68 | 1291 | 213 | 251 | 455 | 5029 | 38572 |
| | (36) | (18) | (10) | (18) | (528) | (79) | (79) | (164) | (4206) | (10305) |
| Ct-AN no. 1-1 | 212 | 329 | 174 | 246 | 2096 | 290 | 798 | 2927 | 15319 | 93479 |
| | (106) | (280) | (74) | (209) | (1187) | (118) | (430) | (1614) | (9291) | (19950) |
| Mt-dAN no. 2-2 | 235 | 141 | 31 | 62 | 3217 | 297 | 263 | 782 | 10545 | 71656 |
| | (20) | (9) | (—) | (4) | (516) | (16) | (38) | (111) | (1725) | (1835) |
| Mt-dAN no. 5-1 | 203 | 248 | 223 | 65 | 2957 | 226 | 587 | 2004 | 8647 | 73453 |
| | (136) | (116) | (—) | (33) | (1736) | (178) | (300) | (1244) | (5235) | (22778) |
| no. 5-2 | 119 | 85 | 25 | 35 | 1101 | 209 | 364 | 2180 | 11583 | 86123 |
| | (39) | (14) | (—) | (2) | (210) | (10) | (122) | (1268) | (732) | (3348) |
| Mt-dAN no. 8-1 | 260 | 240 | 132 | 113 | 2033 | 273 | 463 | 1530 | 25027 | 98662 |
| | (237) | (236) | (182) | (89) | (1152) | (159) | (283) | (814) | (1064) | (26874) |
| no. 8-2 | 262 | 202 | 80 | 95 | 1609 | 248 | 278 | 679 | 7714 | 55401 |
| | (198) | (147) | (52) | (26) | (468) | (113) | (132) | (88) | (2087) | (6076) |

[a]Values in parentheses are standard error (n = 3) (nmol/g.F.W.)

According to the present invention, plants containing free amino acids in a high concentration can be obtained. Thus, crops usable as starting materials and food materials having a high added value are provided. According to the present invention, the whole free amino acid content is increased to 2 to 4-times. Particularly crops containing a very high concentration of at least one of glutamic acid, asparagine, aspartic acid, serine, threonine, alanine and histidine are provided. Thus, crops to be used as starting materials having a high added value and necessitating no further addition of these amino acids are provided. Further, according to the present invention, vegetables which can be directly cooked and which contains a high concentration of glutamic acid accumulated therein, namely food materials having a good taste, can be provided.

In addition, the period for breeding plants containing such free amino acids in a high concentration is remarkably shortened according to the present invention.

What is claimed is:

1. A method of producing a transgenic tomato containing free glutamic acid in a fruit thereof which is at least twice that of the corresponding untransformed tomato, which comprises
   a) transforming a tomato with a genetic construct containing a gene encoding a glutamate dehydrogenase (GDH) having a transit peptide to mitochondria and a marker gene;
   b) selecting or identifying the transgenic tomato based on a character imparted by the marker gene in the genetic construct;
   c) screening the transgenic tomato in which free glutamic acid in the fruit is increased to at least twice that of the corresponding untransformed tomato; and
   d) selecting the transgenic tomato in which free glutamic acid in the fruit is increased to at least twice that of the corresponding untransformed tomato.

2. The method according to claim 1, wherein the genetic construct contains a gene encoding tomato GDH having a transit peptide to mitochondria, wherein said gene is functionally connected to a constitutive promoter or to a fruit-specific promoter.

3. The method according to claim 2, wherein said gene is functionally connected to a constitutive promoter and said constitutive promoter is a CaMV35S.

4. The method according to claim 1, wherein the genetic construct is pT-gdh-4 or pTd-gdh containing the gene encoding tomato GDH gene having a transit peptide to mitochondria.

5. A transgenic tomato produced by the method according to claim 1 and progeny tomatoes thereof, wherein said progeny tomatoes comprise said genetic construct, express the glutamate dehydrogenase gene, and have a free glutamic acid content in the fruit of said progeny tomatoes which is at least twice that of the corresponding untransformed tomato.

6. A method of producing a transgenic tomato having total free amino acids content in a fruit thereof which is at least twice that of the corresponding untransformed tomato, which comprises
   a) transforming a tomato with a genetic construct containing a gene encoding a glutamate dehydrogenase (GDH) having a transit peptide to mitochondria and a marker gene;
   b) selecting or identifying the transgenic tomato based on a character imparted by the marker gene in the genetic construct;
   c) screening the transgenic tomato in which the total content of free amino acids in the fruit is increased to at least twice that of the corresponding untransformed tomato; and
   d) selecting the transgenic tomato in which the total content of free amino acids in the fruit is increased to at least twice that of the corresponding untransformed tomato.

7. The method according to claim 6, wherein the genetic construct contains a gene encoding tomato GDH having a transit peptide to mitochondria, wherein said gene is functionally connected to a constitutive promoter or to a fruit-specific promoter.

8. The method according to claim 7, wherein said gene is functionally connected to a constitutive promoter and said constitutive promoter is a CaMV35S promoter.

9. The method according to claim 6, wherein the genetic construct is pT-gdh-4 or pTd-gdh containing the gene encoding tomato GDH gene having a transit peptide to mitochondria.

10. A transgenic tomato produced by the method according to claim 6 and progeny tomatoes thereof, wherein said progeny tomatoes comprise said genetic construct, express the glutamate dehydrogenase gene, and have a total amino acid content in the fruit of said progeny tomatoes which is at least twice that of the corresponding untransformed tomato.

11. Seeds of the transgenic tomato or progeny according to claim 10, wherein said seed comprise said genetic construct.

12. The method according to claim 2, wherein said gene is functionally connected to a fruit-specific promoter and said fruit-specific promoter is a 2A 11 promoter.

13. The method according to claim 7, wherein said gene is functionally connected to a fruit-specific promoter and said fruit-specific promoter is a 2A11 promoter.

14. A method of producing a transgenic potato containing free glutamic acid in a tuber thereof which is at least twice that of the corresponding untransformed potato, which comprises
   a) transforming a potato with a genetic construct containing a gene encoding a *Aspergillus nidulans* glutamate dehydrogenase (GDH) having a transit peptide to mitochondria and a marker gene;
   b) selecting or identifying the transgenic potato based on a character imparted by the marker gene in the genetic construct;
   c) screening the transgenic potato in which free glutamic acid in the tuber is increased to at least twice that of the corresponding untransformed potato; and
   d) selecting the transgenic potato in which free glutamic acid in the tuber is increased to at least twice that of the corresponding untransformed potato.

15. The method according to claim 14, wherein the genetic construct contains a gene encoding *Aspergillus nidulans* GDH having a transit peptide to mitochondria, wherein said gene is functionally connected to a constitutive promoter.

16. The method according to claim 15, wherein said constitutive promoter is a CaMV35S promoter.

17. The method according to claim 14, wherein the genetic construct is pMt-dAN-gdh or p2Amt-dAN-gdh containing the *Aspergillus nidulans* GDH gene.

18. A transgenic potato produced by the method according to claim 14 and progeny potatoes thereof, wherein said progeny potatoes comprise said genetic construct, express the glutamate dehydrogenase gene, and have a free glutamic acid content in the tuber of said progeny potatoes which is at least twice that of the corresponding untransformed potato.

19. Seeds of the transgenic potato or progeny according to claim 18, wherein said seeds comprise said genetic construct.

20. A method of producing a transgenic potato having total free amino acids content in a tuber thereof which is at least twice that of the corresponding untransformed potato, which comprises
   a) transforming a potato with a genetic construct containing a gene encoding a *Aspergillus nidulans* glutamate dehydrogenase (GDH) having a transit peptide to mitochondria and a marker gene;
   b) selecting or identifying the transgenic potato based on a character imparted by the marker gene in the genetic construct;
   c) screening the transgenic potato in which the total content of free amino acids in the tuber is increased to at least twice that of the corresponding untransformed potato; and d) selecting the transgenic potato in which the total content of free amino acids in the tuber is increased to at least twice that of the corresponding untransformed potato.

21. The method according to claim 20, wherein the genetic construct contains a gene encoding *Aspergillus nidulans* GDH having a transit peptide to mitochondria, wherein said gene is functionally connected to a constitutive promoter.

22. The method according to claim 21, wherein said constitutive promoter is a CaMV35S promoter.

23. The method according to claim 20, wherein the genetic construct is pMt-dAN-gdh or p2Amt-dAN-gdh containing the *Aspergillus nidulans* GDH gene.

24. A transgenic potato produced by the method according to claim 20 and progeny potatoes thereof, wherein said progeny potatoes comprise said genetic construct, express the glutamate dehydrogenase gene, and have a total amino acid content in the tuber of said progeny potatoes which is at least twice that of the corresponding untransformed potato.

25. Seeds of the transgenic potato or progeny according to claim 23, wherein said seed comprise said genetic construct.

26. Seeds of the transgenic tomato or progeny according to claim 5, wherein said seeds comprise said genetic construct.

* * * * *